US006191279B1

(12) United States Patent
Gurjar et al.

(10) Patent No.: US 6,191,279 B1
(45) Date of Patent: Feb. 20, 2001

(54) DIPYRANO-QUINOLINONES USEFUL AS ANTI VIRAL AGENTS AND A PROCESS FOR PREPARING THE SAME

(75) Inventors: Mukund Keshao Gurjar; Gangavaram Vasantha Madhava Sharma; Aindivelu Ilangovan, all of Hyderabad (IN); Ven Narayanan, Bethesda, MD (US)

(73) Assignee: Council of Science & Industrial Research, New Delhi, IN (US)

( * ) Notice: Under 35 U.S.C. 154(b), the term of this patent shall be extended for 0 days.

(21) Appl. No.: 09/321,851

(22) Filed: May 28, 1999

(30) Foreign Application Priority Data

May 29, 1998 (IN) .............................. 1441/DEL/98

(51) Int. Cl.[7] ...................... C07D 491/12; A61K 31/436

(52) U.S. Cl. ................ 546/65; 514/287; 435/5; 435/238; 436/815

(58) Field of Search ................ 514/287; 546/65; 435/5, 238; 436/815

(56) References Cited

U.S. PATENT DOCUMENTS 5,637,589 * 6/1997 Lee et al. .............................. 514/291

OTHER PUBLICATIONS

Yoel Kashman et al., The Calanolides, a Novel HIV–Inhibitory Class of Coumarin Derivatives from the Tropical Rainforest Tree, *Calophyllum lanigerum*[1], J. Med. Chem., vol. 35, pp. 2735–2743, (1992).
Robert A. Newman et al., "Pharmaceutical Properties of Related Calanolide Compounds with Activity against Human Immunodeficiency Virus", Journal of Pharmaceutical Sciences, vol. 87, No. 9, pp. 1077–1080, (1998).

* cited by examiner

Primary Examiner—Charanjit S. Aulakh
(74) Attorney, Agent, or Firm—Finnegan, Henderson, Farabow, Garrett & Dunner, L.L.P.

(57) ABSTRACT

The invention relates to novel dipyrano-quinolinone class of compounds having the general formula:

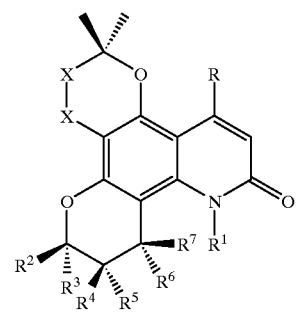

Wherein R is hydrogen, alkyl optionally substituted about C-1 to C-10 alkenyl optionally substituted about C-1 to C-10 with one or more double bounds, alkynyl optionally substituted about C-1 to C-10 with one or more triple bonds, aryl, hetero aryl, carbocyclic aryl, alkyl aryl, alcyclic compounds, C-1 to C-6 alkyl with terminal dialkyl amino group, thio alkyl, hydroxyl alkyl groups;

$R^1$ is H, lower dialkyl amino alkyls such as methyl, ethyl, propyl, and other alkyl groups or b-amino acid moieties, hydroxy alkyl groups having optionally substituted about C-1 to C-10 carbons, acid amides such as aliphatic acids, aromatic acids, sulphonic acids trihalo acids.

x—x is either a carbon-carbon single bond or a carbon-carbon double bond;

$R^2$ and $R^3$, $R^4$ and $R^5$ are each independently hydrogen and methyl there by resulting the cis and trans diastereomers as well as enantiomers;

$R^4$ and $R^5$ are each independently hydrogen and methyl while $R^6$ and $R^7$ are each independently hydrogen and hydroxyl/—$OR^8$, where $R^8$ is independently alkyl, aryl alkyl, amino alkyl, hydroxy alkyl with C-1 to C-10 carbons, sugars which include mono saccharides both in the furanose form as well as pyranose form, amino sugars, disaccharides, amino acids, small peptides through lower alkyl spacer groups, thereby resulting the cis and trans diastereomers as well as enantiomers; and a process for producing the above novel dipyrano-quinolinone class of compounds.

51 Claims, 4 Drawing Sheets under # US 6,191,279 B1

DIPYRANO-QUINOLINONES USEFUL AS ANTI VIRAL AGENTS AND A PROCESS FOR PREPARING THE SAME

FIELD OF THE INVENTION

The present invention relates to novel dipyrano-quinolinone compounds useful as anti-HIV active agents and a process for the preparation of said compounds. The said novel compounds are effective candidate molecules for the treatment of HIV infected patients. The invention further provides novel pharmaceutical compositions comprising such compounds and a process for the preparation of said compositions.

BACKGROUND

Ever since HIV was identified as the etiological cause of AIDS a decade ago, chemotherapy of AIDS has been a very challenging scientific endeavor. Antiviral nucleoside agents such as AZT, ddC, ddI, $d_4T$ and 3TC being Reverse Transcriptase (R.T.) inhibitors are approved for clinical use. Although these nucleoside based drugs can extend the life of the patient, they are associated with several side effects and are not capable of curing the disease.

The urge for the promising RT inhibitors to cure AIDS, resulted in the identification of a group of coumarin derivatives isolated (Ref: M R Boyd et al, J. Med. Chem., 1992, 35, 2735–2743) from genus Calophyllum as HIV-1 specific non-nucleoside inhibitors, among which Calanolide A represented by formula II (X=O) is the most potent and is currently undergoing clinical trials (phase III). The structural formula of the above compound is shown herebelow:

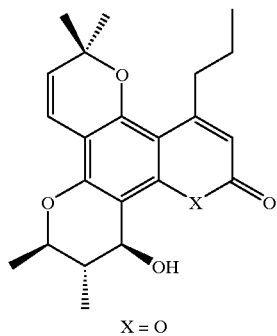

II

X = O

Calanolides, a 'dipyrano-coumarin' class of compounds are active not only against the AZT-resistant strain of HIV-1, but also against virus strains resistant to some other non-nucleoside inhibitors such as TIBO pyridinone, and neviropine. The main drawbacks of this class of compounds are (a) poor solubility of this class of compounds in the physiological medium and (b) lesser stability of the coumarin ring system in biological environment.

It, thus, would be desirable to prepare the New Chemical Entities (NCEs) having calanolide skeleton but with better therapeutic index. In addition, the NCEs are desirable to overcome the problems associated with calanolides such as stability and solubility in the physiological medium as noted above.

Quinolinones are shown to be part structures of several bio-active compounds with profound bio-efficacy. Unlike the lactone bond in coumarins, the lactam bond in quinolinones is highly stable.

This invention, thus deals with the synthesis of novel 'dipyrano-quinolinone' class of compounds related to calanolide structural frame work as NCEs and envisaged to circumvent the problems associated with calanolides and have improved therapeutic indices.

The invention deals with the synthesis of novel and new 'dipyrano-quinolinone' class of compounds that is presented in the form of patent, where the major differences in the structural arrangement is the replacement of coumarin ring oxygen (at position 1) of calanolide structure of formula II (X=O) with nitrogen (at position 1) in the new 'quinolinone' ring system represented by formula II (X=NH). These quinolinone analogues of calanolides are NCEs and are envisaged as potential candidate molecules as anti-HIV agents. The above replacement is not obvious and needs human effort and ingenuity to achieve it. The synthesis and biological activity of 'dipyrano-quinolinone' derivatives is reported for the first time in this patent. The rationale for the synthesis of these 'dipyrano-quinolinones' reported in this specification are as follows:

1. Replacement of oxygen (at position 1) of natural products, calanolides, with nitrogen leads to dipyrano-quinolinones as anti-HIV agents with better therapeutic index.
2. The inherent problems associated with naturally occurring calanolides such as metabolic stability and solubility in physiological medium can be circumvented with the new dipyrano-quinolinone derivatives that are reported in this patent.
3. The derivatisation of water-soluble derivatives of these new chemical entities represented in this patent are easily possible.
4. The metabolic stability is expected to enhance due to the presence of nitrogen atom in the skeleton of dipyrano-quinolinones derivative presented in this patent.
5. The structure activity relationship coupled with positive activity against calanolide resistant strain of HIV virus can be explored due to the presence of nitrogen atom in the dipyrano-quinolinone system.

OBJECTS OF THE INVENTION

It is an object of the invention to synthesise novel class of dipyrano-quinolinone compounds and their analogues having calanolide skeleton but with better therapeutic index.

Another objective of the invention is to provide novel dipyrano-quinolinone and their analogues to overcome the problems associated with calanolides such as stability and solubility in the physiological medium.

Yet another object of the invention is to provide novel quinolinone compounds and analogues having highly stable lactam bond, unlike the lactone bond in coumarins.

A further object of the invention is to provide novel quinolinone compounds with water soluble derivatives.

It is also an objective of the invention to provide novel dipyrano-quinolinone compounds and their analogues containing nitrogen atom in the skeleton, which provides enhanced metabolic stability to the compounds.

Still, another object of the invention provides novel processes for the synthesis of said novel compounds that exhibit significant anti-HIV activity and have a 'dipyrano-quinolinone' framework. These processes utilize commercial reagents and facilitate large-scale manufacture, and provide this new class of totally 'synthetic' entities in sufficient quantities for further biological studies.

DETAILED DESCRIPTION

The Applicant, have now developed synthetic routes for the "New Chemical Entities" having a 'dipyrano-quinolinone' frame work that exhibit significant anti-HIV activity. These short synthetic routes utilize commercial reagents and facilitate large scale manufacture, and provide this new class of totally 'synthetic' entities in sufficient quantities for further biological studies.

The synthetic protocol developed is suitable for the synthesis of compounds of the following formula I:

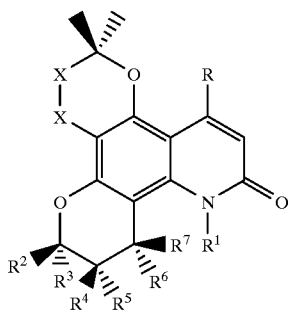

wherein R is hydrogen, alkyl optionally substituted about C-1 to C-10, alkenyl optionally substituted about C-1 to C-10 with one or more double bounds, alkynyl optionally substituted about C-1 to C-10 with one or more triple bonds, aryl, hetero aryl, carbocyclic aryl, alkyl aryl, alcyclic compounds, C-1 to C-6 alkyl with terminal dialkyl amino group, thio alkyl, hydroxy alkyl groups;

$R^1$ is H, lower dialkyl amino alkyls such as methyl, ethyl, propyl, and other alkyl groups or α or β-amino acid moieties, hydroxy alkyl groups having optionally substituted about C-1 to C-10 carbons, acid amides such as aliphatic acids, aromatic acids, sulphonic acids, trihalo acids;

x—x is either a carbon-carbon single bond or a carbon-carbon double bond;

$R^2$ and $R^3$, $R^4$ and $R^5$ are each independently hydrogen and methyl there by resulting in the cis and trans diastereomers as well as enantiomers;

$R^4$ and $R^5$ are each independently hydrogen and methyl while $R^6$ and $R^7$ are each independently hydrogen and hydroxyl-OR, where $R^8$ is independently alyl, aryl alkyl, amino alkyl, hydroxy alkyl with C-1 to C-10 carbons, sugars which include mono saccharides both in the furanose form as well as pyranose form, amino sugars, disaccharides, amino acids, small peptides through lower alkyl spacer groups, thereby resulting in the cis and trans diastereomers as well as enantiomers.

Quinolinones are shown to be part structures of several bio-active compounds with profound bio-efficacy.

This present invention provides class of compounds known as 'dipyrano-quinolinone and their analogues' having basic structural framework of calanolides. The said novel compounds are represented by structural formula I.

The applicants have discovered that the replacement of oxygen at position 1 in the coumarin of ring calanolide structural formula II (X-O) with nitrogen results in novel 'quinolinone' ring compounds represented by formula I (X-NH). These quinolinone compounds and their analogues are potential candidate molecules capable acting as anti-HIV agents. The synthesis and biological activity of "dipyrano-quinolinone" derivatives is reported for the first time in this patent. The intermediate compounds of the invention are useful in therapeutic and other applications.

DEFINITIONS

As used herein, the term 'diastereomeric mixture' refers to a compound in the form of a mixture of cis and trans isomers, while 'enantiomeric mixture' refers to a compound as a racemate.

The term 'alkyl', as used herein unless otherwise specified, refers to a saturated straight chain hydrocarbon of C-1 to C-10 optionally substituted, and specifically include methyl, ethyl, n-propyl, iso-propyl, n-butyl, iso-butyl, pentyl, hexyl, iso-hexyl, 3-methyl pentyl, 2,2-dimethyl butyl, and 2,3-dimethyl butyl.

The term 'alkenyl', as referred to herein and unless otherwise specified, refers to a straight chain hydrocarbon of C-3 to C-10 with at least one double bond, optionally substituted.

The term 'alkyl aryl' refers to an alkyl group that has an aryl substituent. The aryl group can be optionally substituted with any suitable group including but not limited to one or more moieties selected from the groups consisting of halo, hydroxyl, amino, alkyl amino, cyano, alkoxy, aryloxy, nitro.

The term 'lower dialkylamino' refers to an amino group that has one or two lower alkyl substiuents of straight chain hydrocarbons of C-1 to C-3.

The term 'monosaccharides' refers to sugars including but not limited to glucose, galactose, manose, rhamnose, xylose, arabinose, ribose, lyxose, amino sugars—all the sugars both in the furanose form as well as pyranose form, while the term disaccharides refers to sugars including but not limited to lactose, maltose, cellobiose and others.

The term amino acids refers to amino acids including but not limited to alanine, threonine, serine, aspartic acid, lysine, valine, proline and others and small peptides of the mentioned amino acids.

The invention also provides novel processes for the synthesis of the said novel compounds that exhibit significant anti-HIV activity and have a 'dipyrano-quinolinone' framework. These processes utilize commercial reagents and facilitate large scale manufacture, and provide this new class of totally 'synthetic' entities in sufficient quantities for further biological studies.

In one embodiment, the invention provides novel dipyrano-quinolinone compounds of formula 1, where x—x is a C—C single bond or a double bond, $R=R^1=R^3=R^5=R^7=$H, $R^6$=OH, $R^7$=OH, $R^2=R^4$=Methyl, $R=R^1=R^3=R^4=R^6$=H, $R^2=R^5$=Methyl.

In one embodiment, the preferred dipyrano-quinolinones are related to the formula I, wherein x—x is a C—C single or double bond, $R=R^1=R^3=R^5=R^7$=OH, $R^6$=OH, $R^7$=OH, $R^2=R^4$=Methyl, $R=R'=R^3=R^4$=R6=H, $R^2=R^5$=Methyl.

In one embodiment, the invention provides novel dipyrano-quinolinone compounds wherein x—x is a C—C double bond, $R=R^1$=H, $R^2=R^5$=Methyl, $R^7$=OH or $R^2=R^4$=Methyl, $R^6$=OH. The said compounds represented by structural formulae 7 & 8.

In yet another embodiment, the said dipyrano-quinolinone compounds are represented by structural formulae 7,8,21, 22,23,24,25,32,33,34,35,36 and 37.

The invention also provides a novel process for the synthesis of said dipyrano-quinolinone compounds, comprising the steps of:
a) reacting substituted aniline with an acid chloride or 1,3-dioxinone to provide the amides,
b) cyclisation of amides in the presence of acids to provide quinolinones,
c) reacting quinolinone with tigloyl chloride to provide the acylation products,
d) cyclisation of the acylation products in the presence of acid or base to provide the chromanone ring,
e) reacting the chromanone with substituted propargyl chloride to provide chromene, f) reacting the chromanone with suitable reducing agent to provide the new chemical entities the 'dipyrano-quinolinone' class of compounds, if desired, g) hydrogenation of the chromene ring to give the dihydro derivatives, and h) reduction of the dihydro derivatives with reducing agents to get the dihydro analogues.

The present invention provides NCEs as well as pharmaceutical compositions that comprise one or more such compounds. More particularly, this invention describes the compounds of the formula 1, where R is H or methyl or n-Propyl and x—x is a single bond as well as alkenyl moiety both in the diastereomeric as well as enantiomeric mixtures. The NCEs that are prepared in the present invention are used as anti-HIV agents as well as against other viral disorders. The intermediate compounds that are prepared in the present invention are useful synthetic compounds that are useful for other therapeutic applications.

As discussed above, the present invention provides the first synthetic approach to the synthesis of new and novel 'dipyrano-quinolinone' class of compounds of the following formula I:

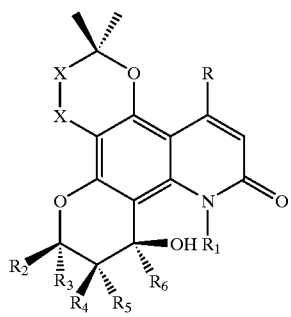

wherein $R^1$, $R^2$, $R^3$, $R^4$, $R^5$, $R^6$, $R^7$, and x—x are as defined above.

Particularly preferred preparative methods of the invention are exemplified in the following Schemes I, II, III, IV and V. The particularly preferred compounds and substituents are depicted in said schemes. It will be understood that the compounds exemplified herein are only representatives for the class of dipyrano-quinolinone compounds.

Scheme I exemplifies as preferred preparative method of the invention that provides compounds of formula I wherein x-x is a double bond, $R=R^1=H$, $R^2=R^5=$Methyl, $R^7=$OH or $R^2=R^4=$Methyl, $R^6=$OH. In the preparative method of this invention a substituted aniline 1 is reacted with cinnamoyl chloride. These two compounds are typically reacted in a suitable solvent like acetone, ethyl methyl ketone and the like in the presence of base for eg: potassium carbonate and the like for a time and temperature sufficient for reaction to provide the amide 2, see example 1, Part 1 below for exemplary reaction.

Scheme I

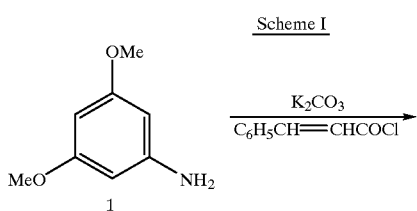

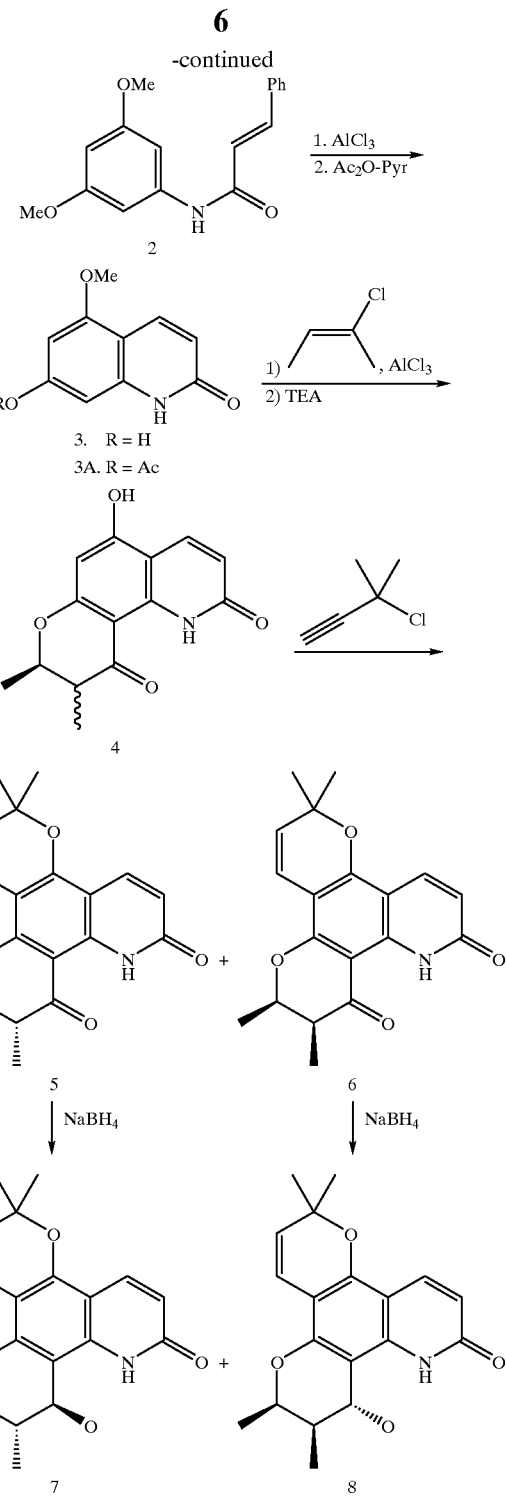

All the compounds reported are racemic

The amide 2, is then reacted with Lewis acid, for eg: aluminium chloride and like in a suitable solvent to provide the quinolinone 3, where in R is represented by hydrogen. See example 1, part 2 for an exemplary reaction conditions. The quinolinone 3 (R=H) can be reacted with acetic anhydride-pyridine to get the diacetate 3A (R=Ac) as exemplified in example 1, Part 3.

The quinolinone represented by formula 3 is further reacted with acid chloride such as tigloyl chloride, that is prepared by the reaction of tiglic acid with thionyl chloride in a conventional way, in the presence of a Lewis acid such as aluminium chloride to get the acylated compound. The ketone was then subjected to cyclisation to get the pyran either under acidic conditions, basic conditions such as triethyl amine or other suitable organic bases in suitable solvent such as chloroform or other solvents to get the compound 4. See example 1, part 4 for exemplary reaction conditions. The compound thus reported in the invention is a diastereomeric and enantiomeric mixture.

Compound 4 was further reacted with 2-chloro-2-methyl-but-3-yne, potassium carbonate, zinc chloride, tetrabutyl ammonium iodide in 2-butanone-DMF as reported for instance (J. Org. Chem. 1995, 60, 2964), to get the mixture of 5 and 6, according to the conditions exemplified in example 1, part 5. The mixture was chromatographically resolved into constituent trans and cis compounds 5 and 6 respectively as a mixture of enantiomers. See example 1, part 5 for the conditions. Finally compounds 5 and 6 were independently reacted with a reducing agent such as sodium borohydride or sodium borohydride-cerium chloride in suitable solvent such as MeOH to get the alcohols 7 and 8 respectively, under the conditions exemplified in example 1, part 6 for 7 and example 1, part 7 for 8.

Scheme II exemplifies a preferred preparative method of the invention that provides compounds of formula 13 and 14, where in R is represented either by a methyl group and by n-propyl group respectively. Thus in Scheme II, aniline 1 can be reacted with the di-oxinone, wherein R is methyl or n-propyl in solvent for eg: xylene and the like at a suitable temperature to provide the amide 9 (R=Me) and 10 (R=n-Pr), where in R is represented by methyl (See example 2, part 1) or n-propyl (See example 3, part 1). Compounds 9 and 10 are independently subjected to cyclisation in the presence of acid reagent for eg: conc. Sulfuric acid and the like at suitable temperature to provide the quinolinone 11 and 12 respectively. For exemplary reaction conditions see example 2, part 2 for 11 and example 3, part 2 for 12. These compounds can be readily deprotected for eg: on reaction with Lewis acid such aluminium chloride and the like in solvent for eg: chlorobenzene and the like to provide the compounds of formula 13 and 14 respectively, where in R is represented by methyl (13) or n-propyl (14) group. See example 2, part 3 for 13 and example 3, part 3 for 14 for exemplary conditions.

Scheme II

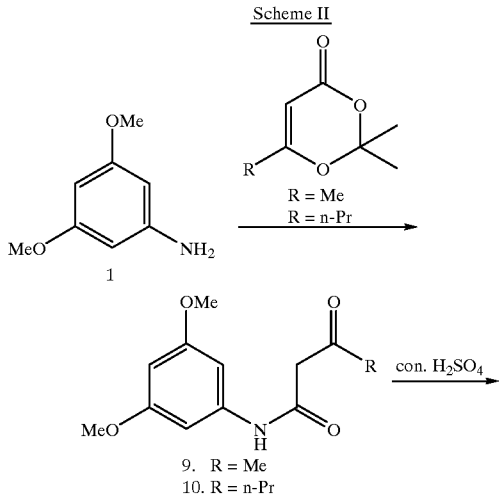

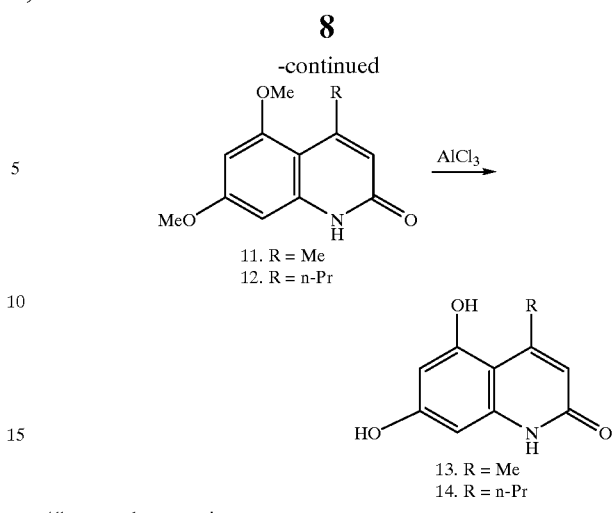

All compounds are racemic

Scheme III further exemplifies the synthetic method of the invention where in compounds 13 and 14, can be reacted with acid chloride such as tigloyl chloride to provide the acylated product which can be further cyclised in to pyran ring under base catalysed conditions for eg: triethyl amine and the like to provide the ketones 15 (R=Me) and 16 (R=n-Pr) as a diastereomeric mixture of compounds, which are inseparable. See example 2, part 4 for 15 and example 3, part 4 for 16.

Compounds of formula 15 and 16 are independently reacted with 3-methyl-3-chlorobutyne in the presence of base for eg: potassium carbonate and the like, reagents such as n-tetrabutyl ammonium iodide, zinc chloride in solvent for eg: 2-butanone-DMF and the like at suitable temperature to provide the chromene as a diastereomeric mixture, which can be resolved into trans compounds of the formula 17 (R-Me) and 18 (R=n-Pr) and cis compounds of the formula 19 (R=Me) and 20 (R=n-Pr). For exemplary reaction conditions for the preparation of 17 and 19 see example 2, part 5 while for 18 and 20, see example 3, part 5.

Scheme III

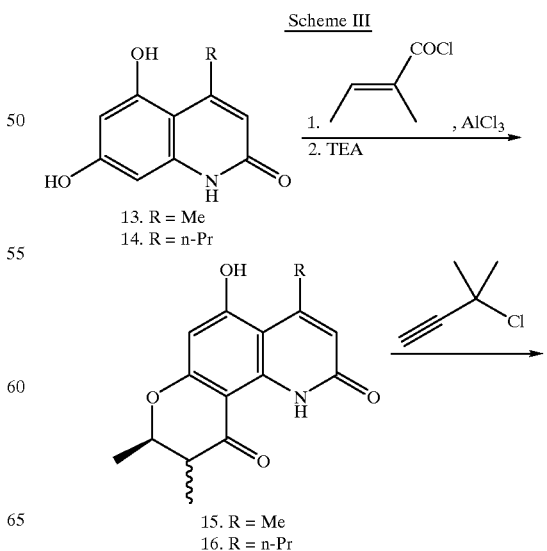

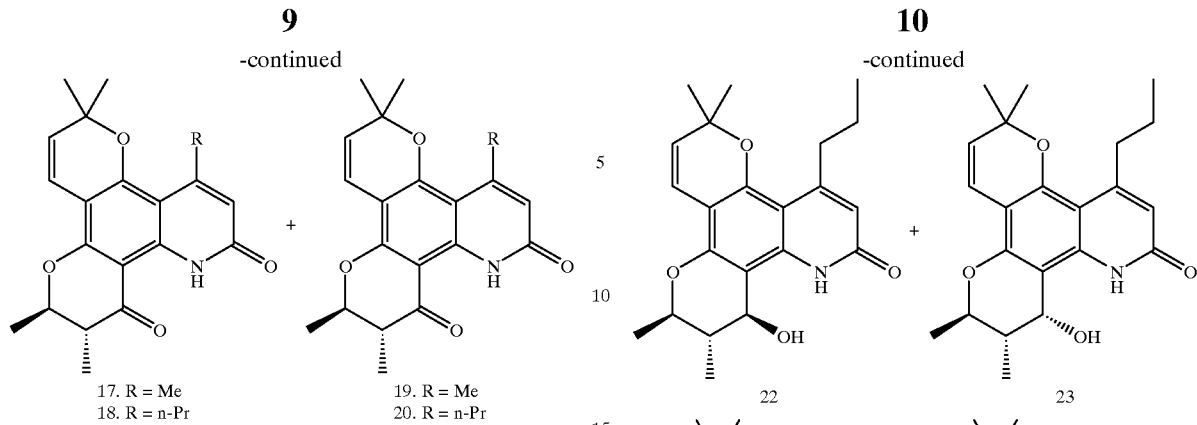

17. R = Me
18. R = n-Pr

19. R = Me
20. R = n-Pr

22

23

19. R = Me
20. R = n-Pr

24. R = Me
25. R = n-Pr

All the compounds reported are racemic

Scheme IV of this invention further exemplifies the conversion of ketones of formula 17, 18, 19 and 20 into NCEs, having carbinols it their structures. The ketones 17 and 19 independently are reduced with suitable reducing agent such as sodium borohydride and like that in a suitable solvent such as MeOH or ethanol to get the alcohols as shown by the formula 21 and 24 respectively. See example 2, part 6 and part 7 for exemplary reaction conditions for the preparation of 21 and 24.

Scheme IV

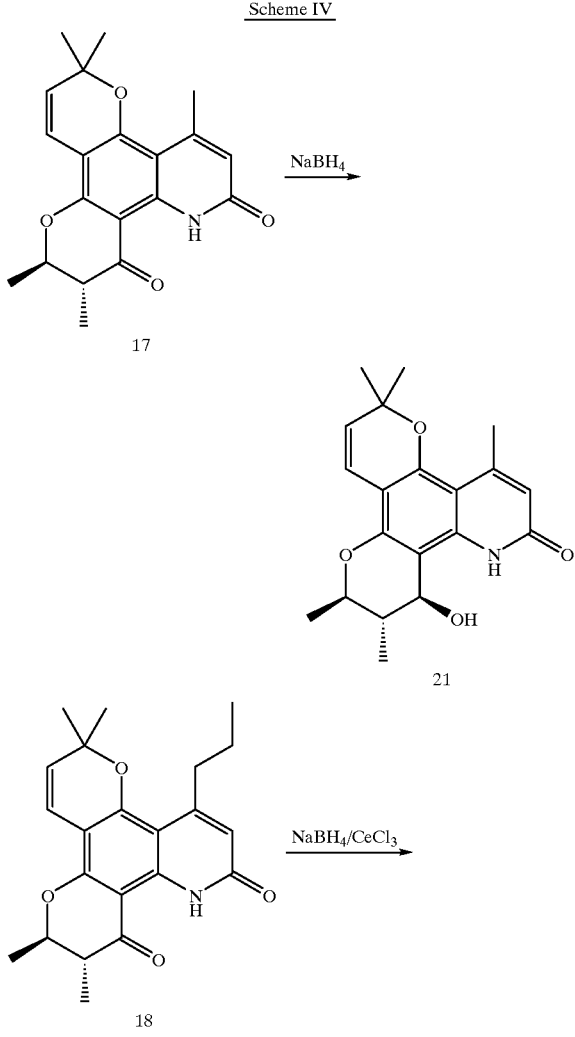

Similarly, ketones 18 and 20 were independently reacted with reducing agents such as sodium borohydride to get the alcohols 22 and 23 from 18, while 25 from 20. See the exemplary reaction conditions in example 3, part 6 for the preparation of 22 and 23 while part 7 for the preparation of 25.

As exemplified in Scheme V, synthetic protocol for several new dihydro derivatives of 'dipyrano-quinolinone' class of compounds have been described, where the compounds are represented by formula 1, wherein x—x is represented by a C—C single bond. The Scheme V exemplifies the preparation of these new and novel 'dihydro' analogues of formula 1, where x—x is a single bond.

As exemplified in the Scheme V, ketones 5 and 6 independently are reacted with suitable catalyst such as Platinum oxide and subjected to hydrogenation at an appropriate pressure in a suitable solvent such as ethyl alcohol to get the dihydro compounds 26 and 27. See example 4, part 1 and example 5, part 1 for the preparation of 26 and 27.

Compounds 26 and 27 were independently reacted with a suitable reducing agent such as sodium borohydride to get the alcohols 32 and 33. For exemplary reaction conditions see example 4, part 2 and example 5, part 2 for the preparation of 32 and 33.

Likewise the ketones 17 and 19 (Scheme V) were independently subjected to catalytic hydrogenation using platinum oxide to get 28 and 29. See example 6, part 1 and example 7, part 1 for the conditions to make 28 and 29. Further 28 and 29 independently can be reacted with reducing reagent such as sodium borohydride to the alcohols 34 and 35. For exemplary reaction conditions see example 6, part 2 and example 7, part 2 for the preparation of 34 and 35.

Scheme V

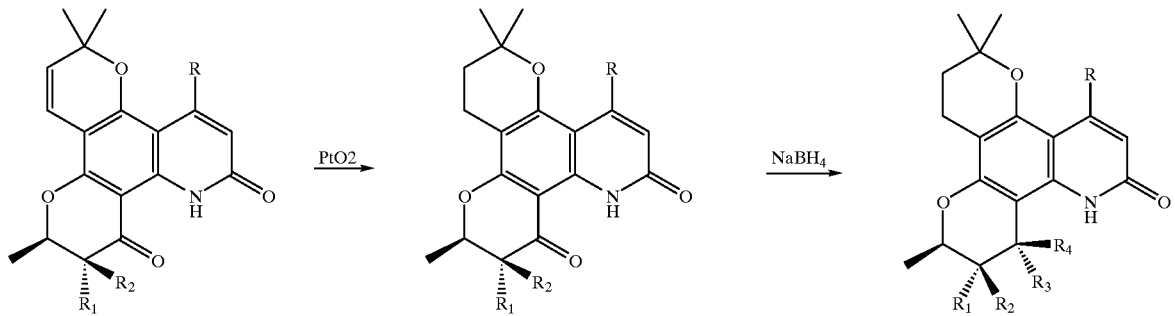

| | | | | | | | | | | | | | | |
|---|---|---|---|---|---|---|---|---|---|---|---|---|---|---|
| 5. R = H, | R₁ = Me, | R₂ = H | 26. R = H, | R₁ = Me, | R₂ = H | 32. R = H, | R₁ = Me, | R₂ = H, | R₃ = H, | R₄ = OH |
| 6. R = H, | R₁ = H, | R₂ = Me | 27. R = H, | R₁ = H, | R₂ = Me | 33. R = H, | R₁ = H, | R₂ = Me, | R₃ = OH, | R₄ = H |
| 17. R = Me, | R₁ = Me, | R₂ = H | 28. R = Me, | R₁ = Me, | R₂ = H | 34. R = Me, | R₁ = Me, | R₂ = H, | R₃ = H, | R₄ = OH |
| 19. R = Me, | R₁ = H, | R₂ = Me | 29. R = Me, | R₁ = H, | R₂ = Me | 35. R = Me, | R₁ = H, | R₂ = Me, | R₃ = OH, | R₄ = H |
| 18. R = n-Pr | R₁ = Me, | R₂ = H | 30. R = n-Pr | R₁ = Me, | R₂ = H | 36. R = n-Pr, | R₁ = Me, | R₂ = H, | R₃ = H, | R₄ = OH |
| 20. R = n-Pr, | R₁ = H, | R₂ = Me | 31. R = n-Pr, | R₁ = H, | R₂ = Me | 37. R = n-Pr, | R₁ = H, | R₂ = Me, | R₃ = OH, | R₄ = H |

All the compounds reported are racemic

In further invention, the ketones 18 and 20 (Scheme V) were independently reacted with platinum oxide to get the dihydro compounds 30 and 31. See example 8, part 1 and example 9, part 1 for the conditions to make 30 and 31. Further 30 and 31 independently can be reacted with reducing reagent such as sodium borohydride to the alcohols 36 and 37. For exemplary reaction conditions see example 8, part 2 and example 9, part 2 for the preparation of 36 and 37.

As exemplified in the schemes I, II, III, IV and V, the synthetic protocols developed by this invention, numerous 'dipyrano-quinolinone' (x—x is represented by a double bond) and 'dihydro dipyrano-quinolinones' (x—x is represented by a single bond) class of compounds represented by formula I can be synthesised. These 'dipyrano-quinolinones' produced by the method of invention are useful for numerous therapeutic applications. Compounds of the invention represented in formula I that have substituted nitrogen in the aromatic ring in place of oxygen, formula 11 (X=O) can be readily prepared. As described in the precedent sections the compounds that are prepared in the present invention are useful for numerous therapeutic applications. In need of treatment, these compounds can be administered by a variety of ways such as orally, parentally, intravenously, subcutaneously and other routes.

The present invention relates with the preparation of NCE's in racemic form. But it often will be preferable to use an optically active or enantiomerically enriched mixture of a chiral compound of the invention for a given therapeutic application. The enantiomerically rich or pure compound is referred to a 'single' enantiomer of the compound or preferably a compound containing more than 92–98 mol % of a single enantiomer.

The synthetic protocol that deals in this invention as exemplified in Schemes I, II, III, IV and V can be effected for the synthesis of 'dipyrano-quinolinone' class of compounds as represented by formula I where in:
$R=R^1=H$, $R 2=R 4=Methyl$, $R3=R5=R 7=H$, $R^5=OH$ and $R=R'=H$, $R^2=R^5=Methyl$, $R^3=R^4=R^6=H$, $R^7=OH$, x-x is both a C-C single bond as well as double bond is synthesised.

Similarly compound having formula I can be synthesised where in: $R=R^2=R^4=Methyl$, $R^1=R^3=R^5=R^7=H$, $R^6=OH$ and $R=R^2=R^5=Methyl$, $R^1=R^3=R^4=R^6=H$, $R^7=OH$, x-x is both a C—C single bond as well as double bond is synthesised.

Similarly compound having formula I can be synthesised where in: $R=n$-propyl, $R^2=R^4=Methyl$, $R^1=R^3=R^5=R^7=H$, $R^6=OH$ and $R=n$-propyl, $R^2=R^5=Methyl$, $R^1=R^3=R^4=R^6=H$, $R^7=OH$, x-x is represented both by a C-C single bond as well as double bond is synthesised.

The synthetic protocol that deals in this invention as exemplified in the Schemes I, II, III, IV and V can be utilised for all the 'dipyrano-quinolinones' that are shown above as formula I and numerous other analogues can be similarly made using the synthetic protocol that is described in this invention for the first time.

Biological activity

The invention deals with the synthesis of novel and new 'dipyrano-quinolinone' class of compounds of formula 1, that are structurally related to calanolides (formula II, X=O), a non-nucleoside class of anti-HIV agents. Calanolides are in the advanced stage of biological evaluation as anti-H IV agents in clinical trials (phase III). These new chemical entities (NCEs), the dipyrano-quinolinone class of new and novel compounds that are provided in this invention are of potential therapeutic value as "Candidate Molecules". The compound of the formula II (X=NH) is screened for anti-HIV activity. The above compound of formula II (X=NH), reported in this invention is shown to have equal amount of activity against HIV infected cell lines as that observed for calanolides in the in vitro preliminary screening studies. The $IC_{50}$, $EC_{50}$ and TI values of both calanolides and the 'new dipyrano-quinolinone chemical entities' of formula II (X=NH) described in the present invention have equal and more protecting capacity against the HIV infection. The results of the preliminary screening of the New Chemical Entities that are prepared in the present invention based on the 'dipyrano-quinolinones', aginst HIV is shown in the FIGS. 1, 2, 3 and 4. These results indicate that the NCE's prepared in the present invention have almost equal amount of activity as that of the calanolides (formula II, X=O) that are isolated from the natural sources.

Figure 1:
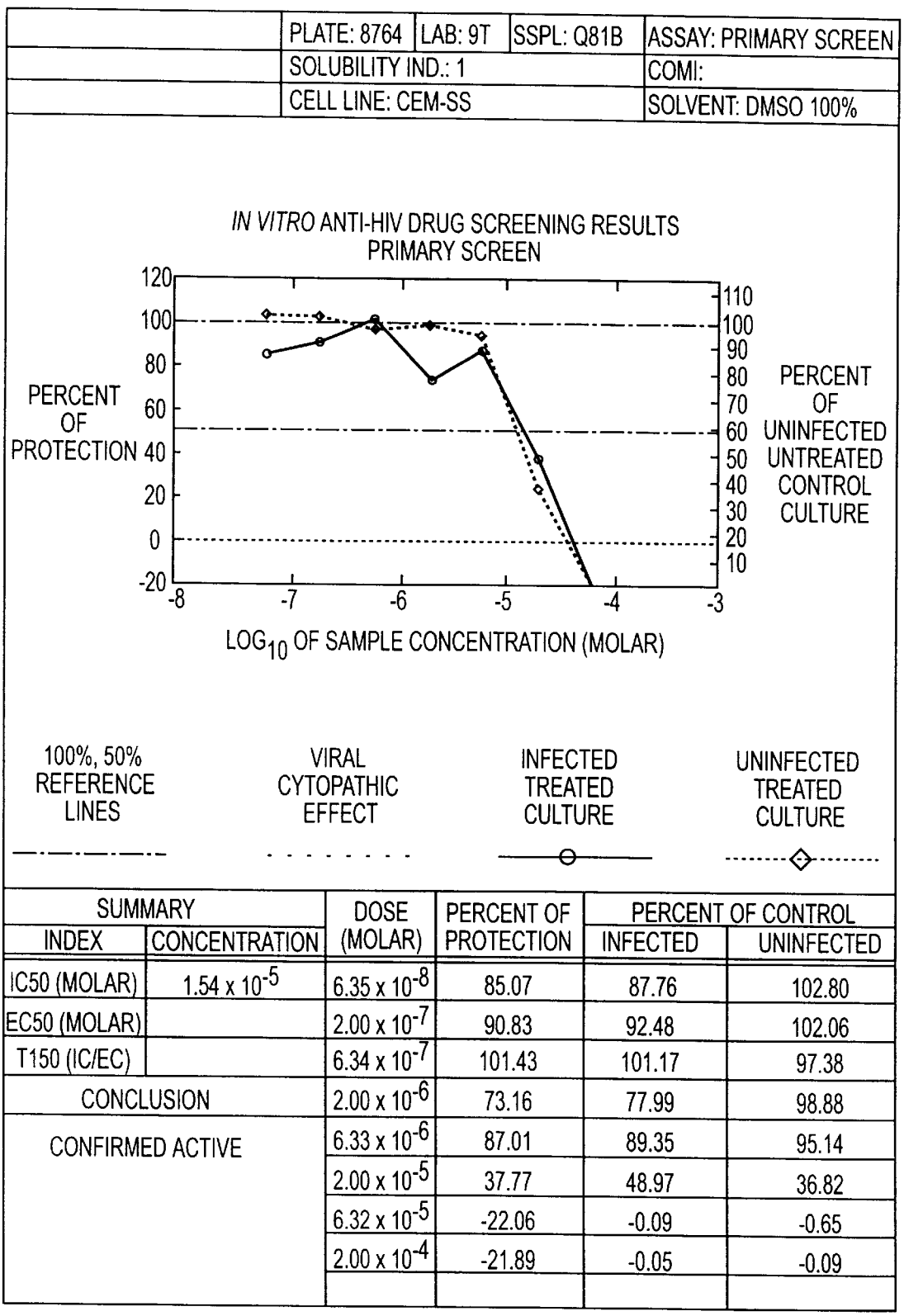
FIGS. 1 to 4 relate to In Vitro anti-HIV drug screening results (primary screen).
Figure 2:
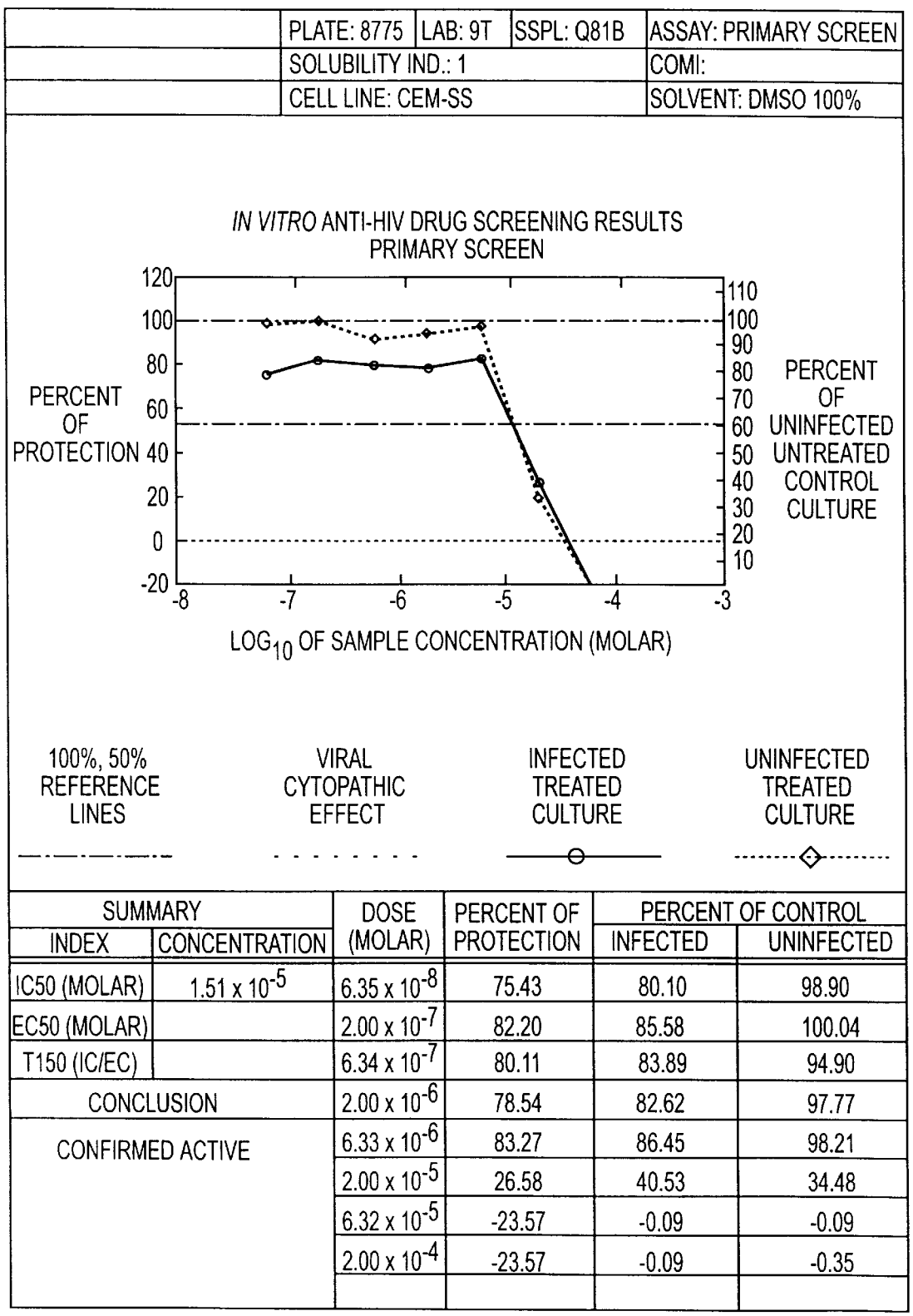
Figure 3:
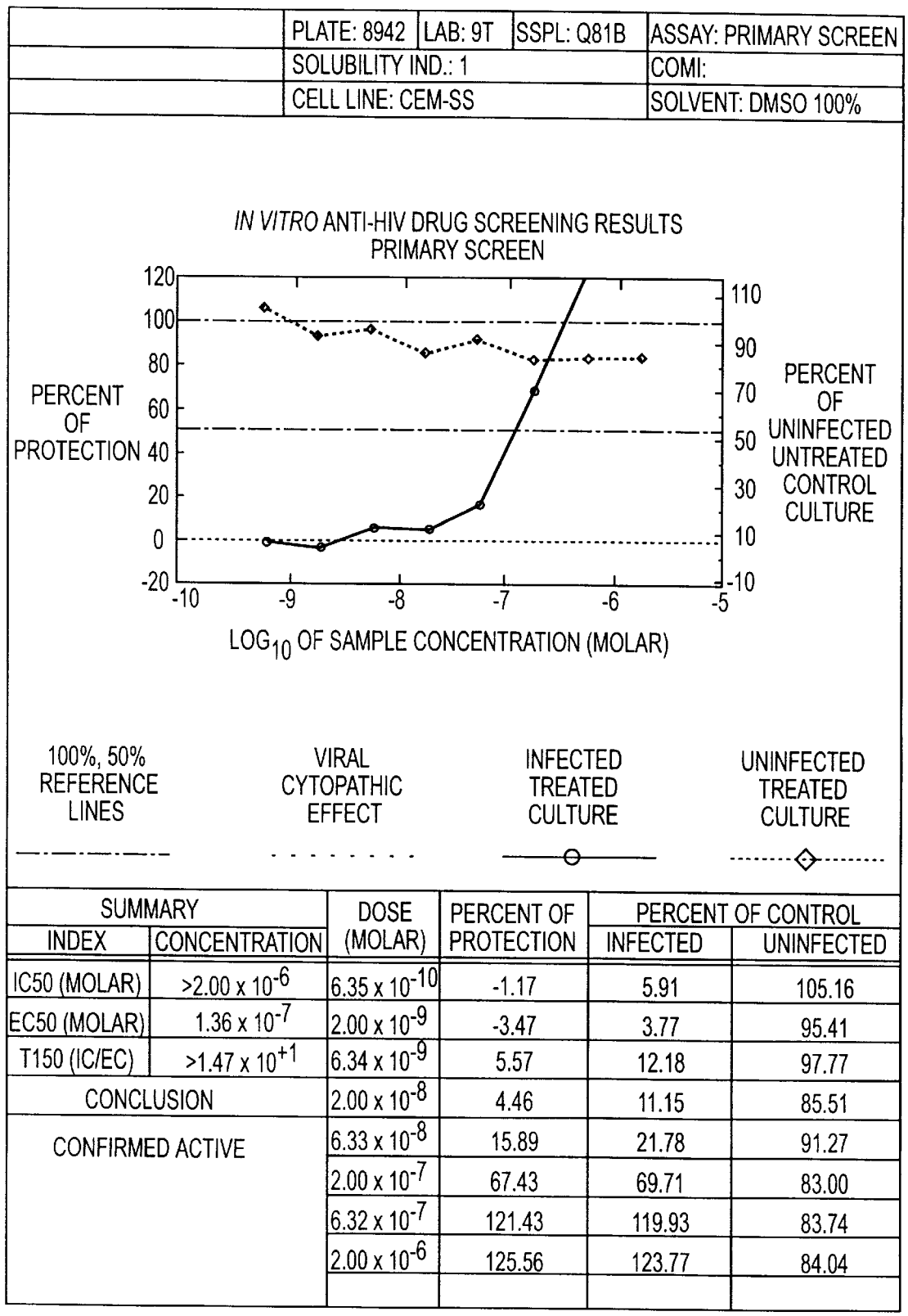
Figure 4:
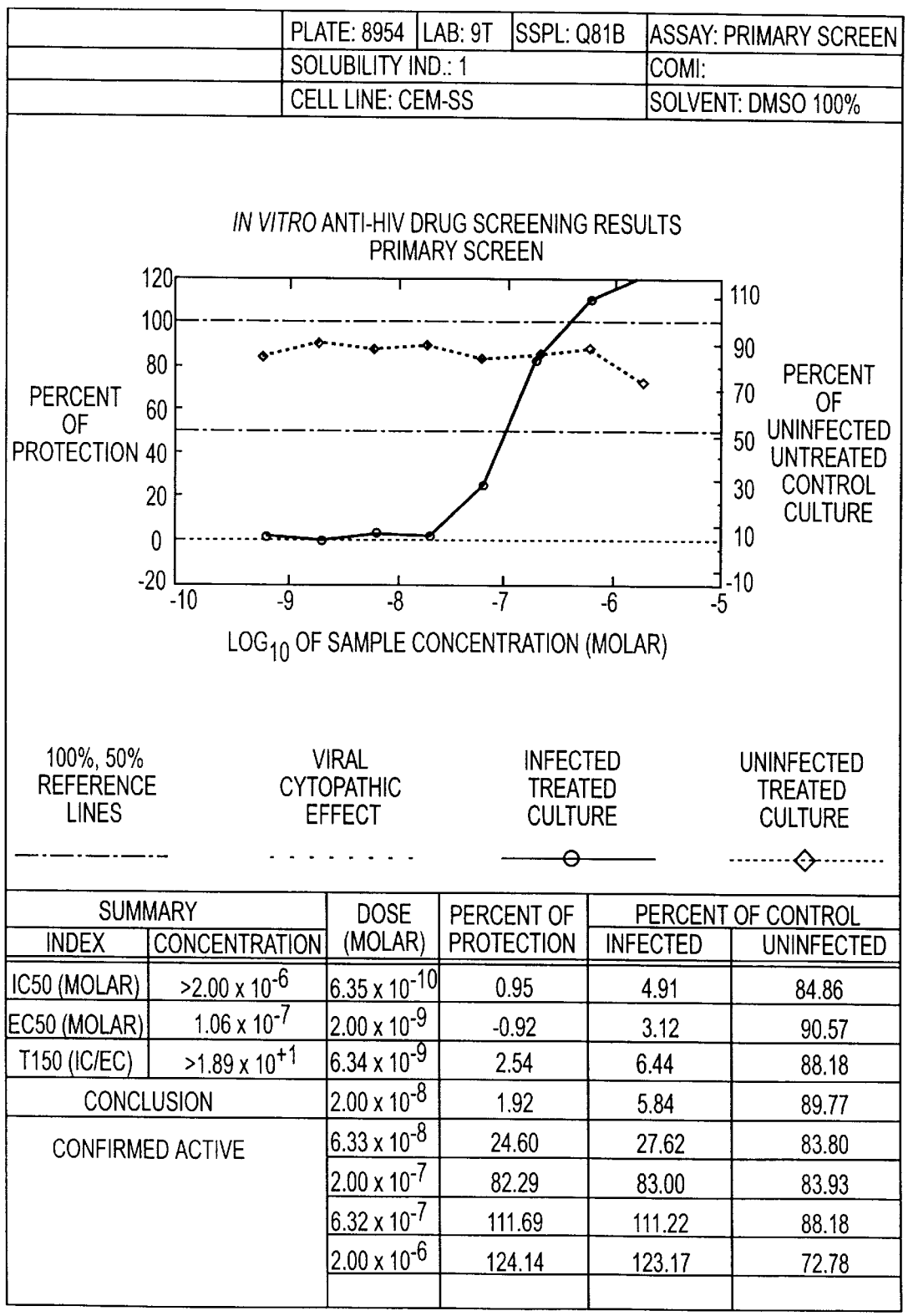

As indicated earlier, Calanolides are a novel HIV-inhibitory class of dipyrano coumarin derivatives that were isolated from the tropical rain forest tree calophyllum lanigerum. These compounds act as potent non-nucleoside inhibitors of HIV-1 reverse transcriptase Calanolides (formula-1 where N-R'=O, R=n-Pr; J. Med. Chem. 1992, 35, 2735–2743), inophyllum (Formula-1 where N-R'=O, R=ph), cordatolides (Formula-1 where N-R'+O, R=Me: Phytochem 1998, 49, 995 and Plant Medica 1997, in press) have shown potent anti HIV-1 RT activity. Further studies conducted on calanolide A (Formula-1 where N-R'=O, R=n-Pr, x-x=C—C double bond) and its dihydro derivative (Formula-1 where N-R'=O, R=n-Pr, x-x =C-C single bond) revealed (J. Pharm. Sci, 1998, 87, 1077) that dihydro derivative may be a reasonable choice of further preclinical development of possible phase I evaluation based on the available structure-activity data, IICT has developed dipyrano quinolinone class of NCE's to circumvent the problems that are associated with the parent natural product, and one such NCE (compound No. 22) has shown anti HIV-1 RT activity. The biological studies revealed the mean therapeutic index of 86 for calanolide A. While the NCE prepared at IICT has shown a mean therapeutic index value of 1 2&, indicative of the superior activity for the new compound compared to the natural one from the structure-activity relationship as well as from the activity data obtained for compound No. 22, it is expected that several NCE's, both the saturated as well as unsaturated ones that are reported in the present patent to be potential anti-HIV active compounds.

The expected target compounds are as follows. Compound No. 7, 8, 21–25, 32–37.

The following non-limiting examples are illustrative of the invention.

EXAMPLE 1

Preparation of 8-Hydroxy -2,2,6,7-tetramethyl-7,8,9,10-tetrahydro-2H,6H-dipyrano [2,3-f: 2,3-h]quinolin-10-one (Scheme I; 7 and 8)

Part 1: 1N- (3, 5-dimethoxyphenyl)-3-phenyl-(E)-2-propenamide (Scheme I; 2)

A mixture of 3,5-dimethoxy aniline 1 (10.3 g, 67.5 mmol) and potassium carbonate (13.9 g, 101.2 mmol) was taken in acetone-water (150 mL, 1:2) and cooled to 5° C. Cinnamoyl chloride (12.2 g, 67.5 mmol) (prepared by treatment of a solution of cinnamic acid (10 g, 67.5 mmol) in benzene (40 mL) with thionyl chloride (8 g, 67.5 mmol) at reflux temperature for 1 h.) was added in 15 min. to reaction mixture while maintaining temperature below 5° C. Reaction mixture was stirred below 5° C. for 30 min. and allowed to raise to room temperature over a period of 30 min. (TLC, hexane:ethyl acetate, 7:3, $R_f$=0.4). The reaction mixture was diluted with water (100 mL) and solid separated was filtered. The solid was washed with water (2×50 ml) dried under vacuum to afford 1N-(3,5-dimethoxyphenyl)-3-phenyl-(E)-2-propenamide (2) (18.1 g) in 95% yield as a off white solid. M.P. 142–145° C.

IR (neat): 3280, 3025, 3200, 2960, 2945, 2830, 2850, 1670,1616 cm$^{-1}$

1H NMR (CDCl$_3$, 200 MHz): δ3.8 (s, 6H, 2CH$_3$), 6.2 (s, 1H, ArH), 6.53 (d, 1H, J=16.4 Hz, PhC$\underline{H}$=CH), 6.8 (s, 2H, 2ArH), 7.35 (m, 3H, 3ArH), 7.5 (m, 2H, 2ArH), 7.73 (d, 1H, J=16.4 Hz, PhCH=C$\underline{H}$).

MSEI: m/z 283 (M$^+$, 12), 206 (18), 153 (48), 131 (100)

Part 2:5,7-Dihydroxy-1,2-dihydro-2-quinorinone (Scheme I; 3)

A solution of compound 2 (19.0 g, 67.1 mmol) in chlorobenzene (120 mL) was taken in a 500 mL round bottom flask equipped with a mechanical stirrer and a reflux condenser. Aluminium chloride (44.6 g, 335.6 mmol) was added in portions over a period of 10 min. The reaction mixture was heated at 130° C. for 3 h and cooled to room temperature (TLC chloroform: methanol 9:1, $R_f$=0.2). Poured into crushed ice (1 Kg) and stirred at room temperature for further 30 min. The solid separated was filtered and washed with water till neutral to pH. The solid was then washed with hexane (2×50 mL) and dried at 100° C. for 1 h to furnish 5,7-dihydroxy-1,2-dihydro-2-quinolinone (3, 10 g) in 92% yield as a dark brown solid. M.P.>300° C. The quinolinone obtained was further characterised as its diacetate.

Part 3: 5, 7-Diacetoxy-1,2-dihydro-2-quinolinone (Scheme I; 3A)

A solution of compound 3 (1 g, 5.6 mmol) in pyridine (5 mL) in a RB flask was treated with acetic anhydride (1.12 g, 11.2 mmol) at 0° C. and allowed to stir at room temperature overnight. Pyridine was removed under reduced pressure and residue obtained was subjected to chromatographic purification (silica gel, ethyl acetate:hexane 6:4) to furnish 5,7-diacetoxy-1,2-dihydro-2-quinolinone (3A, 1.38 g) in 95% yield as a pale yellow solid. M.P. 230–232° C.

IR (Neat): 2982, 2930, 2870, 1760,1680 cm$^{-1}$.

$^1$H NMR (CDCl$_3$+DMSO-d$_6$, 200 MHz): δ 2.32 (s, 3H, CH$_3$), 2.4 (s, 3H, CH$_3$), 6.5 (d, 1H, J=8.3 Hz, H3), 6.78 (d, 1H, J=2.0 Hz, H-6), 7.03 (d, 1H, J=2.0 Hz, H-8), 7.25 (bs, 1H. NH), 7.72 (d, 1H, J =4.3 Hz, H-4).

MSEI: m/z 261 (M$^+$, 8), 219 (18), 177 (100), 149 (15)

Part 4: (±) 5-Hydroxy-8, 9-dimethyl-1,8,9,10-tetrahydro-2H-pyrano[2,3-h]-quinoline-2,10-dione (Scheme I; 4)

A mixture of compound 3 (11.5 g, 65 mmol), aluminium chloride (43.2 g, 324 mmol) and CS$_2$ (200 mL) was taken in a 500 mL round bottom flask equipped with a mechanical stirrer and a reflux-condenser. The reaction mixture was heated at 50° C. for 30 min. Nitrobenzene (60 mL) was added dropwise in 30 min and stirred for additional 30 min to get a homogeneous mixture. Tigloyl chloride (11.5 g, 97.5 mmol) in nitrobenzene (20 mL) was added dropwise in 30 min. and stirred at 50° C. for a period of 48 h. The reaction mixture was cooled to room temperature after completion of reaction (TLC chloroform: methanol, 9:1, $R_f$=0.4), poured on crushed ice (.500 g) and stirred for 30 min. The solid separated was filtered and washed with water till neutral to pH. It was dried under vacuum to get dark brown solid. The solid was dispersed in chloroform (200 mL) and treated with triethylamine (10 mL, 7.2 g, 72 mmol) while being stirred at room temperature. After 12h reaction mixture was filtered and residue was extracted with hot chloroform (3×200 mL). Combined chloroform extracts were evaporated to get grey colour residue. The residue was purified by column chromatography (silica gel, 60–120 mesh, chloroform: methanol 19:1) to afford (±) 5-hydroxy-8, 9-dimethyl-1,8,9,10-tetrahydro-2H-pyrano [2, 3-h3-quinoline-2, 10-dione (4, 2.2 9) in 27.5% yield. M.P. 275–277° C.

IR (Neat): 3450, 3200, 3000, 2940, 1620 cm$^{-1}$.

$^1$H NMR (CDCl$_3$, 200 MHz): δ 1.09–1.22 (m, 3H, CH$_3$), 1.38 (d, 1.8H, J=6.6 Hz, CH$_3$) 1.45 (d, 1.2H, J=6.6 Hz, CH$_3$), 2.52–2.7 (m, 4H, CH$_3$ and H-9), 4.3 (dq, 0.6H, J=6.6 Hz and 11.4 Hz, H-8), 4.68 (dq, 0.4H, J=3.5 Hz and 6.5 Hz, H-6), 6.20–6.21 (2s, 1H, H-6), 6.38 (d, 1H, J=10 Hz, H-3), 8.0 (d, 1H, J=10.0 Hz, H-4), 12.4 (br s, 1H, NH).

MSEI: m/z 259 (MI, 6), 203 (6), 101 (36), 86 (100)

Part 5: (±) 2,2,6,7-Tetramethyl-7,8,9,10-tetrahydro-2H, 6H-dipyrano[2,3-f :2,3-h]quinoline-8,10-dione (Scheme I; 5 and 6)

To a solution of compound 4 (1.85 g, 7.14 mmol) in 9:1 mixture of 2-butanone and DMF (1 9 mL) taken in a 100 mL round bottom flask equipped with a reflux condenser, 2-methyl-3-butyn-2-chloride (3.6 g, 35.7 mmol), potassium carbonate (2.4 g, 8.9 mmol), tetrabutylammonium iodide (2.6 g, 7.14 mmol) and zinc chloride (1.21 g, 8.9 mmol) were added sequentially. The reaction mixture was then refluxed for 12h to see the complete consumption of compound 4 (TLC, hexane:ethyl acetate, 7:3 $R_f$=0.4). The reaction mixture was cooled to room temperature, water (20 mL) added and 2-butanone was evaporated under reduced pressure. The residue was extracted with ethyl acetate (3×30 mL), and combined organic layers were washed with water (20 mL), dried ($Na_2SO_4$) and evaporated to get oily residue. The residue obtained was purified through column chromatography on (silica gel, finer than 200 mesh, hexane:ethyl acetate 9:1) to afford (±) 2,2,6,7-tetramethyl-7,8,9,10-tetrahydro-2H, 6H-dipyrano[2,3-f:2,3-h]quinoline-8,10-dione (5, 0.85 g) in 36.5% yield as a white solid. M.P. 177–179° C.

IR (KBr): 3225, 3000, 2950, 1672, 1640, 1625 $cm^{-1}$.

$^1$H NMR ($CDCl_3$, 200 MHz): δ 1.23 (d, 3H, J=7.4 Hz, $OH_3$), 1.5 (s, 3H, $CH_3$), 1.52 (s, 3H, $CH_3$), 1.59 (d, 3H, J=7.4 Hz, $CH_3$), 2.61 (dq, I H, J=6.0 Hz, 1 1.2 Hz, H-7), 4.26 (dq, 1 H, J=6.1 Hz, 1 1.4 Hz, H-6), 5.58 (d, I1H, J=1 0.2 Hz, H-8), 6.44 (d, 1 H, J=10.0 Hz, H-11), 6.61 (d, 1H, J=10.3 Hz, H-4), 7.95 (d, 1H, J=10.3 Hz, H-1 2).

MSEI: m/z 326 ($M^+$1, 32), 311 (100), 255 (66). HRMS: calculated for $C_{19}H_{20}NO_4$ 326.1392.33, observed 326.139986.

Second eluted was (+) 2,2,6,7-tetramethyl-7,8,9,10-tetrahydro-2H, 6H-dipyrano[2,3-f: 2,3-h]quinoline-8,100dione (6, 0.34 g) in 14.6% yield as a white solid. M.P. 165–166° C.

$^1$H NMR ($CDCl_3$, 200 MHz): δ 1.19 (d, 3H, J=7.3 Hz, $CH_3$), 1.45 (d, 3H, J=7.3 Hz, $CH_3$), 1.50–1.52 (2s, 6H, $2CH_3$), 2.82 (dq, 1 H, J=3.4 Hz and 7.0 Hz, H-7), 4.67 (dq, 1H, J=3.4 Hz and 6.5 Hz, H-6), 5.58 (d, 1H, J=9.6 Hz, H-7), 6.45 (d, 1H, J=9.8 Hz, H-1 1), 6.59 (d, 1H, J=9.8 Hz, H-4), 7.94 (d, 1H, J=9.9 Hz, H-12), 12.4 (brs, 1H, NH). Part 6: (±) 8-Hydroxy-2,2,6,7-tetramethyl-7,8,9,10-tetrahydro-2H,6H-dipyrano[2,3-f: 2,3-h]quinolin-10-one (Scheme I; 7)

To a stirred solution of compound 5 (0.19, 0.307 mmol) in ethanol (1 ml) cooled to 0° C., sodium borohydride (0.011 g, 0.307 mmol) was added in portions. The reaction mixture was allowed to raise to room temperature over a period of 1 h. After completion of reaction (TLC, hexane : ethyl acetate, 6:4, $R_f$=0.2)), water (2 mL) was added and extracted with ethyl acetate (3×5 mL). The combined organic layers were successively washed with water (4 ml), brine (4 mL), dried ($Na_2SO_4$) and evaporated. The crude product obtained by evaporation of solvent was subjected to chromatographic purification (silica gel,60–120 mesh, hexane: ethyl acetate 1:8) to afford product (±) 8-hydroxy-2,2,6,7-tetramethyl-7, 8,9,10-tetrahydro-2H, 6H-dipyrano[2, 3-f: 2,3-h]quinolin-10-one (7, 71 mg) in 71% yield as a white solid. M.P. 198–199° C.

IR (KBr): 3200, 2975,2925,1648 $cm^{-1}$.

$^1$H NMR ($CDCl_3$, 200 MHz): δ 1.23 (d, 3H, J=6.6 Hz, $CH_3$), 1.42–1.52 (2s, 9H, $3CH_3$), 2.05 (dq, 1 H, J=6.4 Hz, 9.4 Hz, H-7), 3.95 (dq, 1 H, J=6.4 Hz, 9.4 Hz, H-6), 4.67 (d, 1H, J=8.6 Hz, H-8), 5.52 (d, I H, J=10.0 Hz, H-3), 6.3 (d, 1H, J=9.6 Hz, H-11), 6.6 (d, 1H, J=9.9 Hz, H-4), 7.98 (d, 1H, J=9.6 Hz, H-12).

MSEI: m/z 309 ($M^+$ —$H_2O$, 40), 294 (100), 208 (10).

HRMS calculated for $C_{18}H_{21}NO_4$ 327.147058, observed 327.148287.

Part 7: (±) Hydroxy-2,2,6,7-tetramethyl-7,8,9,10-tetrahydro-2H, 6H-dipyrano 12,3-f: 2,3-h]quinolin-10-one (Scheme I; 8)

Compound 6 (0.2 g, 0.614 mmol) in ethanol (2 ml) was treated with sodium borohydride (0.022 g, 0.0614 mmol) for 1h and the same work up procedure described for the preparation of 7 was adopted in the present case and the crude product obtained was purified by column chromatography (silica gel, 60–120 mesh, hexane:ethyl acetate 1:8) gave (±) hydroxy-2,2,6,7-tetramethyl-7,8,9,10-tetrahydro-2H, 6H-dipyrano [2, 3-f: 2,3-h]quinolin-10-one (8, 0.15 g) in 74% yield as a white solid. M.P. 172–175° C. $^1$H NMR ($CDCl_3$, 200 MHz): δ 1.08 (d, 3H, J=6.8 Hz, $CH_3$), 1.41 (d, 3H, J=6.7 Hz, $CH_3$), 1.46 (s, 6H, $2CH_3$), 2.32 (dq, I H, J=3.6 Hz, 6.0 Hz, H-7), 4.4 (dq,1 H, J=3.6 Hz, 6.0 Hz, H-6), 5.4 (d,1 H, J=5.4 Hz, H-8), 5.47 (d, 1 H, J=10.0 Hz, H-3), 6.39 (d, 1H, J=10.0 Hz, H-1 1), 6.6 (d, 1H, J=9.9 Hz, H4), 8.08 (d, 1H, J=9.6 Hz, H-12), 11.8 (brs, 1H, NH).

EXAMPLE 2

Preparation of (±) 8-Hydroxy-2,2,6,7,12-pentamethyl-7, 8,9,10-tetrahydro-2H, 6H-dipyrano[2,3-f: 2,3-h]quinolin-10-one (Scheme II; 21 and 24)

Part 1: 1N-(3, 5-dimethoxyphenyl)-3-oxo-butanamide (Scheme II; 9)

A solution of 3,5-dimethoxy aniline 1 (5 g, 32.6 mmol) in xylene (20 mL) was taken in a 100 mL round bottom flask equipped with a reflux condenser and a dropping funnel and heated at 130° C. under nitrogen atmosphere. 2,2,6-trimethyl4H-1, 3-dioxin-4-one (4.64 g, 32.6 mmol) was then added dropwise for 25 min. Heating was continued at 125–130° C. for additional 3 h (TLC hexane : ethyl acetate, 6:4 $R_f$=0.3). The reaction mixture was cooled to 50° C. and xylene was removed under vacuum to get oily residue. The residue obtained was purified by column chromatography (silica gel hexane:ethyl acetate 4:1) to get product 1 N-(3, 5-dimethoxyphenyl)-3-oxo-butanamide (9, 7.2 g) in 93% yield as an oily liquid.

IR (Neat): 3310, 3000, 2920, 2825, 1720,1667 $cm^{-1}$ $^1$H NMR ($CDCl_3$, 200 MHz): δ 2.3 (s, 2H, $CH_3$), 3.5 (s, 2H, $CH_2$), 3.73 (s, 6H, $2CH_3$), 6.17 (s, 1H, ArH), 6.72–6.73 (2s, 2H, 2ArH), 9.1 (brs, 1H, NH)

MSEI: m/z 237 ($M^+$, 61),179 (22),153 (68),124 (23).

Part 2: 5,7-Dimethoxy-4-methyl-1,2-dihydro-2-quinolinone (Scheme II; 11)

Compound 9 (13.9 g, 58.6 mmol) was taken in a 100 mL round bottom flask and cooled to 0° C. Conc. $H_2SO_4$ (35 mL, 657 mmol) was added dropwise for 10 min at 0° C. and allowed the reaction mixture to reach room temperature over a period of 30 min. After completion of the reaction (TLC hexane : ethyl acetate 1:1, $R_f$=0.3) it was poured into water (200 mL) and solid separated was filtered, the solid was washed with water till neutral to pH and dried under vacuum to give product 5,7-dimethoxy4-methyl-1,2-dihydro-2-quinolinone (11, 12.5 g) in 97.6% yield as a solid. M.P. 239–240° C.

IR (Neat): 3400, 3000, 2950, 2875, 1665, 1636, 1607 $cm^{-1}$ $^1$H NMR ($CDCl_3$, 200 MHz); δ 2.65 (s, 3H, $CH_3$), 3.86 (s, 3H, $OCH_3$), 3.92 (s, 3H, $OCH_3$), 6.2 (s, 1 H, H-3), 6.24 (s, 1H, H-6), 6.48 (s, 1H, H-8), 12.36 (brs, 1H, NH)

MSEI : m/z 219 ($M^+$, 100), 203 (10), 190 (16), 176 (25).

Part 3: 5,7-Dihydroxy-4-methyl-1,2-dihydro-2-quinolinone (Scheme II; 13)

To a stirred solution of compound 11 (12.5 g, 57.07 mmol) in chlorobenzene (100 mL), aluminium chloride (37 g, 285.3 mmol) was added in portions over a period of 10 min and heated at 100° C. overnight (TLC chloroform:

methanol 9:1, $R_f$=0.2). The reaction mixture was then cooled to room temperature, poured on crushed ice (300 g) and stirred well for 30 min. The solid separated was filtered washed with water till neutral to pH. It was then washed with hexane (50 mL) and dried to give product 5,7-dihydroxy-4-methyl-1,2-dihydro-2-quinolinone (13, 10.5 g) in 96% yield as a dark brown solid. M.P. >300° C.

IR (KBr): 3200,2960,1665,1631 cm$^{-1}$

Part 4: (±) 5-Hydroxy-4,8,9-trimethyl-1,8,9,10-tetrahydro-2H-pyrano[2, 3-h]-quinoline-2,10-dione (Scheme III; 15)

A mixture of compound 13 (11.2 g, 58.6 mmol), carbon disulfide (220 mL) and nitrobenzene (80 mL) in a RBF was treated with AlCl$_3$ (38.93 g, 293 mmol) followed by tigloyl chloride (8.33 g, 70.3 mmol). After completion of reaction (TLC chloroform:methanol, 9:1, $R_f$=0.4) the reaction was worked up as described for preparation of compound 4 and further treatment with triethylamine (8.2 mL, 64.4 mmol) in chloroform (200 mL) as described for 4 gave a residue after work up. The residue on purification by column chromatography (silica gel, 60–120 mesh, chloroform : methanol, 19:1) furnished (±) 5-hydroxy4,8,9-trimethyl-1,8,9,10-tetrahydro-2H-pyrano[2,3-h]-quinoline-2,10-dione (15, 1.9 g) in 21% yield as a solid. M.P. 300° C.

IR (KBr): 3434,2980,1670,1610 cm$^{-1}$ $^1$H NMR (CDCl$_3$+DMSO-d$_6$, 200 MHz): δ 1.15–1.33 (m, 3H, CH$_3$), 1.45 (d, 1.2H, J=7.0 Hz, CH$_3$), 1.52 (d, 1.8H, J=7.0 Hz, CH$_3$), 2.48–2.68 (m, 4H, CH$_3$ and H-9), 4.27 (dq, 0.6H, J=6.1 Hz, 11.2 Hz, H-8), 4.66 (dq, 0.4H, J=3.2 Hz, 6.4 Hz, H-8), 6.13–6.15 (2s, 1H, H-6), 6.30 (s, 1H, H-3), 12.8 (brs, 1H, NH).

MSEI: m/z 273 (M$^+$, 39), 250 (12), 217 (100), 189 (15), 161 (14).

Part 5: (±) 2, 2, 6, 7, 12-Pentamethyl-7,8,9,10-tetrahydro-2H, 6H-dipyrano[2,3-f: 2,3-h]quinoline-8,10-dione (Scheme III; 17 and 19)

A round bottom flask containing compound 15 (0.9 g, 3.29 mmol) in 9:1 mixture of 2-butanone and DMF (19 mL) was sequentially treated with potassium carbonate (1.13 g, 8.2 mmol), 2-methyl-3-butyn-2-chloride (1.68 g, 16.4 mmol) tetrabutylammonium iodide (1.2 g, 3.29 mmol) and zinc chloride (0.56 g, 4.1 mmol) as described for the preparation of 5 and 6. The residue obtained after work up was purified by column chromatography (silica gel, finer than 200 mesh, hexane:ethyl acetate, 9:1), first to afford (±) 2,2,6,7,12-pentamethyl-7,8,9,10-tetrahydro-2H,6H-dipyrano[2,3-f: 2,3-h]quinoline-8,10-dione (17, 0.335 g) in 30% yield, as a white solid.

M.P. 167–169° C.

IR (KBr): 3448,3200,1676,1644 cm$^{-1}$.

$^1$H NMR (CDCl$_3$, 200 MHz): 5 1.22 (d, 3H, J=7.1 Hz, CH$_3$), 1.48–1.62 (m, 9H, 3CH$_3$), 2.5–2.78 (m, 4H, CH$_3$ and H-7), 4.26 (dq, 1 H, J=6.3 Hz, 11.4 Hz, H-6), 5.52 (d, 1H, J=10.0 Hz, H-7), 6.22 (s, 1H, H-1 1), 6.6 (d, 1H, J=9.9 Hz, H-4), 12.82 (brs, 1H, NH). MSEI: m/z 339 (M+, 35), 324 (100), 168 (46). HRMS: calculated for C$_{20}$H$_{21}$NO$_4$ 339.146181, observed 339.147058.

Second eluted was (±) 2,2,6,7,12-pentamethyl-7,8,9,10-tetrahydro-2H, 6H-dipyrano-[2,3-f: 2,3-h]quinoline-8,10-dione (19, 0.16 g) in 14.4% yield as a syrupy liquid.

$^1$H NMR (CDCl$_3$, 200 MHz): δ 1.2 (d,3H, J=6.9 Hz, CH$_3$), 1.48 (d,3H, J=6.4 Hz, CH$_3$), 1.50 (s, 3H, CH$_3$), 1.51 (s, 3H, CH$_3$), 2.55–2.65 (m, 4H, CH$_3$ and H-7), 4.68 (dq, 1 H, J=2.8 Hz, 6.1 Hz, H-6), 5.54 (d,1H, J=9.9 Hz,H-7), 6.6 (d, 1H, J=9.9 Hz, H-8), 12.8 (bs, 1H, NH).

Part 6: (±) 8-Hydroxy-2,2,6,7,12-pentamethyl-7,8,9,10-tetrahydro-2H, 6H-dipyrano[2, 3-f: 2,3-h]quinolin-10-one (Scheme IV; 21)

A solution of compound 17 (0.1 g, 0.295 mmol) in ethanol (2 mL) in a RBF was treated with sodium borohydride (0.011 g, 0.295 mmol) for 1h. Usual work up as described for the preparation of 7 and purification of the crude product by column chromatography (silica gel, 60–120 mesh, hexane : ethyl acetate, 1:8) gave (±) 8-hydroxy-2,2,6,7,12-pentamethyl-7,8,9,10-tetrahydro-2H, 6H-dipyrano[2, 3-f: 2,3-h]quinolin-10-one (21, 0.081 g) in 80% yield as a white solid. M.P. 167–169° C.

IR(KBr): 3255,2975,2920,1650 cm$^{-1}$ $^1$H NMR (CDCl$_3$, 200 MHz): δ 1.2 (d, 3H, J=6.9 Hz, CH$_3$), 1.42–1.52 (m, 9H, 3CH$_3$), 2.02 (m, 1H, H-7), 2.55 (s, 3H, CH$_3$), 3.9 (dq, 1H, J=6.1 Hz, 11.2 Hz, H-6), 4.56 (d, 1H, J=8.5 Hz, H-8), 5.49 (d, 1H, J=9.6 Hz, H-3), 5.94 (s, 1H, H-1 1), 6.6 (d, 1H, J=9.4 Hz, H-4).

MSEI: m/z 323 (M$^+$-H$_2$O, 32), 308 (100), 147 (10).

HRMS: calculated for C$_{20}$H$_{21}$NO$_3$ 323.152144, observed 323.152195.

Part 7: (±) 8-Hydroxy-2,2,6,7,12-pentamethyl-7,8,9,10-tetrahydro-2H, 6H-dipyrano[2,3-f: 2,3-h]quinolin-10-one (Scheme IV; 24)

A solution of compound 19 (0.1 g, 0.295 mmol) in ethanol (2 mL) was treated with sodium borohydride (0.011 g, Q.295 mmol) for 1h. The crude product obtained after work up as described for 7 and chromatographic purification (silica gel, 60–120 mesh, hexane:ethyl acetate, 1:8) gave (±) 8-hydroxy-2,2,6,7,12-pentamethyl-7,8,9,10-tetrahydro-2H, 6H-dipyrano[2,3-f: 2,3-h]quinolin-10-one (24, 0.076 g) in 75% yield as a white solid. M.P. 185–188° C.

$^1$H NMR (CDCl$_3$, 200 MHz): δ 1.07 (d, 3H, J=7.0 Hz, CH$_3$), 1.42 (d, 3H, J=7 Hz, CH$_3$), 1.5 (s, 6H, 2CH$_3$), 2.32 (dq, 1 H, J=2.9 Hz, 6.0 Hz, H-7), 2.76 (s, 3H, CH$_3$), 4.36 (dq6 1(H, J=2.9 Hz, 6.0 Hz, H-6), 5.33 (d, 1H, J=8.9 Hz, H-8), 5.46 (d, HH, J=10.0 Hz, H-3), 6.17 (s, 16H, H-1), 6.63 (d, 18H, J=10.0 Hz, H-4).

EXAMPLE 3

Preparation of (±) 8-Hydroxy-2,2,6,7-tetramethyl-12-propyl-7,8,9,10-tetrahydro-2H, 6H-dipyrano [2, 3-f: 2,3-h] quinolin-10-one (Scheme IV: 22, 23 and 25)

Part 1: 5N-(3, 5-dimethoxyphenyl)-3-oxohexanamide (Scheme II; 10)

3,5-Dimethoxy aniline 1(14.5 g, 92.5 mmol) in xylene (50 mL) was treated with 2,2-dimethyl-6-propyl-4H-1,3-dioxinone (17.3 g, 101.7 mmol) worked up and purified as described for 9 to afford e N-(3, 5-dimethoxyphenyl)-3-oxohexanamide (10, 18.8 g) in 77% yield as an oily liquid.

IR (Neat): 3325, 2960, 2925,1710,1650 cm$^{-1}$ $^1$H NMR (CDCl$_3$, 200 MHz): 0.96 (t, 3H, J=6.2 Hz, CH$_3$), 1.65 (m, 2H, CH$_2$), 2.54 (t, 2H, J=6.2 Hz, CH$_2$), 3.5 (s, 2H, CH$_2$), 3.8 (s, 6H, 2 -OCH$_3$), 6.2 (s, I H, ArH), 6.75–6.76 (2s, 2H, 2ArH).

MSEI: m/z 265 (M$^+$, 62), 203 (20), 186 (10), 179 (21), 153 (100)

Part 2: 5,7-Dimethoxy-4-propyl-1,2-dihydro-2-quinolinone (Scheme 11; 12)

Compound 10 (19 g, 71.69 mmol) was treated with Conc. H$_2$SO$_4$ (48 mL, 901 mmol) for 30 min. as described for II after usual work up afforded 5,7-dimethoxy-4-propyl-1,2-dihydro-2-quinolinone (12,159) in 90% yield as a white solid. M.P. 193–196° C.

IR (Neat): 1670, 1625, 1605 cm$^{-1}$.

$^1$H NMR (CDCl$_3$+DMSO-d$_6$, 200 MHz): δ 1.0 (t, 3H, J=6.3 Hz, CH$_3$), 1.54–1.74 (m, 2H, CH$_2$), 2.9 (t, 2H, J=6.3 Hz, CH$_2$), 3.8 (s, 3H, -OCH$_3$), 3.9 (s, 3H, —OCH$_3$), 6.15 (s, 1H, H-3), 6.22 (s, 1H, H-6), 6.5 (s, 1H, H-8), 11.7 (bs, 1H, NH).

MSEI: m/z 247 (M$^+$, 95), 230 (22), 219 (44), 204 (100)

Part 3: 5, 7-Dihydroxy-4-propyl-1,2-dihydro-2-quinolinone (Scheme II; 14)

A solution of compound 12 (12 g, 48.5 mmol) in chlorobenzene (100 mL) was treated with AlCl$_3$ (25 g, 194.5 mmol) for 3 hr. and usual work up as described for 13 afforded 5,7-dihydroxy-4-propyl-1,2-dihydro-2-quinolinone (14, 10 g) in 97% yield as a dark brown solid. M.P. >300° C.

IR (KBr): 3280, 3220, 3140, 1650 cm$^{-1}$.

Part 4: (±) 5-Hydroxy-8,9-dimethyl-4-propyl-1,8,9,10-tetrahydro -2H-pyrano [2,3-h]quinolin-2,10-dione (Scheme III; 16)

A mixture of compound 14 (7.0 g, 32.5 mmol), carbon disulfide (140 mL) and nitrobenzene (45 mL) was treated with AlCl$_3$ (21.6 g, 162 mmol) at 50° C. and tigloyl chloride (4.6 g, 39 mmol) was added. After completion of the reaction (TLC, chloroform:methanol, 9:1, R$_f$=0.4), treatment with triethylamine (4.97 mL, 3 .61 g, 35.7 mmol) in chloroform (1 50 mL) as described for 4, gave a residue. Purification of residue by column chromatography (silica gel, 60–120 mesh, chloroform: methanol, 9:1) furnished (±)5-hydroxy-8,9-dimethyl-4-propyl-1,8,9,10-tetrahydro-2H-pyrano [2,3-h]quinolin-2,10-dione (16, 1.39) in 23% yield as a solid. M.P. 295–296° C.

IR (Neat): 3425, 2958, 2920, 2860, 1595 cm$^{-1}$ $^1$H NMR (CDCl$_3$, 200 MHz): δ 1.0 (t, 3H, J=7.2 Hz, CH$_3$), 1.16–1.3 (m, 3H, CH$_3$), 1.44 (d, 1.2H, J=6.5 Hz, CH$_3$ ), 1.52 (d, 1.8H, J=6.7 Hz, CH$_3$ ), 1.65 (m, 2H, CH$_2$ ), 2.5–2.7 (m, 1 H, H-9), 2.95 (t, 2H, J=6.3 Hz, CH$_2$), 4.28 (dq, 1.8H, J=6.4 Hz, 1 1.4 Hz, H-8), 4.68 (dq, 1.2 H, J=3.4Hz, 6.2 Hz, H-8), 6.12 (s, 1H, H-6), 6.20 (s, NH), 11.32 (br s, 1H), 12.88 (br s, 1H).

MSEI: m/z 301 (M$^+$, 46), 286 (15), 273 (41), 245 (12), 217 (15)

Part 5: (±) 2,2,6,7-Tetramethyl-12-propyl-7,8,9,10-tetrahydro-2H, 6H-dipyrano[2,3-f: 2,3-h]quinoline-8,10-dione (Scheme III: 18 and 20)

Compound 16 (2.0 g, 6.64 mmol) in 9:1 mixture of 2-butanone and DMF (35 mL) was sequentially treated with K$_2$CO$_3$ (2.28 g, 16.6 mmol), 2-methyl-3-butyn-2-chloride (3.4 g, 33.2 mmol), nBu$_4$NI (2.44 g, 6.6 mmol) and ZnCl$_2$ (1.030 g, 8.3 mmol). The reaction was carried out and worked up as described for 5 and 6. The residue obtained was purified by column chromatography (silica gel, 60–120 mesh, hexane:ethyl acetate, 8:2) first to get (±) 2,2,6,7-tetramethyl-12-propyl-7,8,9,10-tetrahydro-2H, 6H-dipyrano [2,3-f: 2,3-h]quinoline-8,10-dione (18, 0.672 g), in 27.5% yield as a white solid, M.P.120–121° C.

IR (KBr): 3180, 2986, 2963, 2892, 1690,1664 cm$^{-1}$.

$^1$H NMR (CDCl$_3$, 200 MHz): δ 1.04 (t, 3H, J=7.1 Hz, CH$_3$), 1.22 (d, 2H, J=6.9Hz, CH$_3$),1.54 (s, 3H, CH$_3$),1.58 (s, 3H$_1$, CH$_3$), 1.69–1.78 (m, 5H, CH$_3$ and CH$_2$), 2.6 (dq, 1H, J=6.9 Hz, 11.1 Hz, H-7), 2.91 (t, 2H, J=6.9Hz), 4.3 (dq, 1H, J=6.3Hz, 11.1 Hz, H-6), 5.54 (d, 1H, J=10.1 Hz, H-3), 6.24 (s, 1H, H-11), 6.62 (d, 1H, J=10.1 Hz, H4), 12.95 (bs, 1H, NH).

MSEI: m/z 367 (M$^+$, 22), 352 (100), 296 (39). HRMS: calculated for C$_{22}$H$_{25}$NO$_4$ 367.178359, observed 367.176729.

Second eluted was (±) 2,2,6,7-tetramethyl-12-propyl-7,8,9,10-tetrahydro-2H, 6H-dipyrano[2,3-f: 2,3-h]quinoline-8,10-dione (20, 0.416 g) in 14.6% yield as a syrupy liquid.

$^1$H NMR (CDCl$_3$, 200 MHz): δ 1.05 (t, 3H, J=7.3 Hz, CH$_3$), 1.22 (d, 2H, J=7.1 Hz, CH$_3$), 1.50 (d, 3H, J=7.1Hz, CH$_3$), 1.61 (s, 3H, CH$_3$), 1.62 (s, 3H, CH$_3$), 1.63–1.69 (m,2H,CH$_2$), 2.68 (dq, 11H, J=3.4 Hz, 6.0 Hz, H-7), 2.95 (t, 3H, J=8.1 Hz, CH$_2$), 4.69 (dq, 1H J=3.0 Hz, 6.2 Hz, H-6), 5.55 (d,1 H. J=10.2 Hz, H-3), 6.28 (s, 1 H H-11), 6.64 (d, 1H, J=10.2 Hz, H-4), 12.9 (bs, 1t, NH).

Part 6: (±) 8-Hydroxy-2,2,6,7-tetramethyl-12-propyl-7,8, 9,10-tetrahydro-2H, 6H-dipyrano [2, 3-f, 2,3-h]quinolin-10-one (Scheme IV; 22 and 23)

A mixture of compound 18 (0.1 g, 0.272 mmol) and CeCl3.7H$_2$0 (0.202 g, 0.544 mmol) in ethanol (3 mL) was taken in a round bottom flask and stirred at room temperature for 2 h. The reaction mixture was cooled to −30° C., sodium borohydride (0.01 g, 0.272 mmol) was added slowly and stirred at −30° C. for 10 h (TLC, hexane: ethyl acetate, 3:2, R$_f$=0.2). The reaction mixture was allowed to rise to room temperature, quenched with water (3 mL) and extracted with ethyl acetate (3×5 mL). Combined organic layers were washed with brine (5 mL), dried (Na$_2$SO$_4$) and evaporated to get a gummy residue. The residue was purified by column chromatography (silica gel, finer than 200 mesh, hexane:ethyl acetate, 3:7) and first eluted was (±) 8-hydroxy-2,2,6,7-tetramethyl-12-propyl-7,8,9,10-tetrahydro-2H, 6H-dipyrano[2,3-f: 2,3-h]quinolin-10-one (22, 0.048 g) in 47.5% yield as a white solid.

M.P. 164–166° C.

IR (neat): 3250, 2988,2945,2875,1660 cm$^{-1}$.

$^1$H NMR (CDCl$_3$, 200 MHz): δ 1.00 (t, 3H, J=7.3 Hz, CH$_3$), 1.19 (d, 3H, J=6.6 Hz, CH$_3$), 1.45–1.52 (m, 9H, J=7.1 Hz, 3CH$_3$), 1.59 (dq, 1 H, J=6.0 Hz, 11.5 Hz, H-7), 2.92 (m, 2H, CH$_2$), 3.91 (dq, 1 H, J=6.4 Hz, 9.4 Hz, H-6), 4.59 (d, 1 H, J=9.0 Hz, H-8), 5.49 (d, 1H, J=9.9 Hz, H-3), 6.10 (s, 1H, H-11), 6.63 (d, 1H, J=9.9 Hz, H-4).

MSEI: m/z 352 (M$^+$-OH, 17), 351 (M+- H$_2$0, 17), 336 (100), 284 (10).

HRMS: calculated for C$_{22}$H$_{27}$NO4 369.194009, observed 369.192293.

Second eluted was (±) 8-hydroxy-2,2,6,7-tetramethyl-12-propyl-7,8,9,10-tetrahydro-2H, 6H-dipyrano[2, 3-f: 2, 3-h]quinolin-10-one.(23, 0.006 g) in 6% yield.

$^1$H NMR (CDCl$_3$, 200 MHz): δ 1.02 (t, 3H, J=7.3 Hz, CH$_3$), 1.2 (d, 3H, J=6.5 Hz, CH$_3$), 1.42 (d, 3H, J=6.6 Hz, CH$_3$ ), 1.49 (s, 3H, CH$_3$), 1.50 (s, 3H, CH$_3$), 1.59–1.78 (m,2H,CH$_2$), 2.9–3.08 (m, 2H, CH$_2$), 4.25 (dq, 1H, J=10.5 Hz, 6.2 Hz, H-6), 4.78 (d, 1H, J=3.1 Hz, H-8), 5.49 (d, 1H, J=9.8 Hz, H-3), 6.18 (s, 1H, H-1 1), 6.64 (d, 1H, J=9.9 Hz, H-4).

Part 7: (±) 8-Hydroxy-2, 2, 6, 7-tetramethyl-12-n-propyl-7, 8, 9, 10-tetrahydro-2H, 6H-dipyrano[2,3-f: 2, 3-h] quinolin-10-one (Scheme IV; 25)

Compound 20 (0.15 g, 0.408 mmol) in ethanol (3 mL) was treated with sodium borohydride (0.015 g, 0.408 mmol) and worked up as described for 7 to afford (±) 8-hydroxy-2,2,6,7-tetramethyl-7,8,9,10-tetrahydro-2H, 6H-dipyrano[2, 3-f: 2, 3-h]quinolin-10-one (25, 0.11 g) in 73% yield as a white solid. M.P. 1 85–188° C.

$^1$H NMR (CDCl$_3$, 200 MHz): δ 1.05 (t, 3H, J=7.2 Hz, CH$_3$), 1.12 (d, 3H, J=6.5 Hz, CH$_3$), 1.4 (d, 3H, J=6.5 Hz, CH$_3$), 1.46 (s, 3H, CH$_3$), 1.48 (s, 3H, CH$_3$), 1.63 (m, 2H, CH$_2$), 2.35 (m, $_1$ H, H-7), 2.95 (m, 2H, CH$_2$), 4.31 (dq, 1 H. J=3.0 Hz, 6.1 Hz, H-8), 5.34 (d, 1H, J=5.6 Hz, H-8), 5.47 (d, 1H, J=10.0 Hz, H-3), 6.19 (s, 1H, H-11), 6.62 (d, 1H, J=10.0 Hz, H-4).

EXAMPLE 4

Preparation of (±) 8-Hydroxy-2, 2, 6, 7-tetramethyl-3,4,7,8,9,10-hexahydro-2H, 6H-dipyrano[2,3-f: 2, 3-h]quinolin-10-one (Scheme V; 32)

Part 1: (±) 2,2,6,7-Tetramethyl-3,4,7,8,9,10-hexahydro-2H, 6H-dipyrano [2,3 - f: 2,3-h]quinoline-8, 10-dione (Scheme V; 26)

To a solution of compound 5 (0.17 g, 0.5 mmol) in ethanol (2 ml), $PtO_2$ (0.017 g) was added and subjected to hydrogenation at 15 psi for 1 h. The reaction mixture was filtered and concentrated to get solid residue. The residue obtained was purified through column chromatography (silica gel, 60–120 mesh, hexane:ethyl acetate, 1: 6) to get (±) 2,2,6,7-tetramethyl-3,4,7,8,9,10-hexahydro-2H, 6H-dipyrano [2,3-f: 2,3-h]quinoline-8,10-dione (26) (0.130 g) in 72% yield as a white solid. M.P. 148–150° C.

$^1$H NMR ($CDCl_3$, 200 MHz): δ 1.31 (d, 3H, J=7.0 Hz, $CH_3$ ), 1.43 (s, 3H, $CH_3$), 1.45 (s, 3H, $CH_3$), 1.61 (d, 3H, J=6.9 Hz), 1.9 (t, 2H, J=6.5 Hz, $CH_2$), 2.5–2.67 (m, 3H, $CH_2$ and H-7), 4.3 (dq, 1 H, J=6.3 Hz, 11.9 Hz, H-6), 6.24 (d, 1 H, J=9.5 Hz, H-11), 7.98 (d, 1H, J=9.7 Hz, H-1 2), 12.42 (bs, 1H).

MSEI: m/z 327 ($M^+$, 25), 272 (22) 256 (9), 228 (13), 216 (30).

Part 2: (±) 8-Hydroxy-2,2,6,7-tetramethyl-3,4,7,8,9,10-hexahydro-2H, 6H-dipyrano[2,3-f: 2,3-h]quinolin-10-one ( Scheme V; 32)

Compound 26 (0.05 g, 0.153 mmol) in ethanol (0.5 ml) was treated with sodium borohydride (0.005 g, 0.153 mmol) as described for 7 and worked up in the usual way. The residue after purification by column chromatography (silica gel, 60–120 mesh, hexane:ethyl acetate, 9:1) afforded product (±) 8-hydroxy-2,2,6,7-tetramethyl-3,4,7, 8,9,10-hexahydro-2H, 6H-dipyrano[2,3-f: 2,3-h]quinoline-8,10-dione (32, 0.024 g) in 48% yield as a white solid. M.P. 190–195° C.

$^1$H NMR ($CDCl_3$, 200 MHz): δ 0.9 (d, 3H, J=7.0 Hz, $CH_3$), 1.38–1.48 (2s, 9H, $3CH_3$), 1.8 (t, 2H, J=6.6 Hz, $CH_2$), 2.31 (dq, 1H, J=6.0 Hz, 11.8 Hz, H-7), 2.68 (t, 2H, J=6.8 Hz, $CH_2$), 3.9 (dq, 1 H, J=6.0 Hz, 11.7 Hz, H-6), 4.74 (d, 1 H, J=9.9 Hz, H-8), 6.37 (d, 1H, J=9.8 Hz, H-11), 8.16 (d, 1H, J=10.0 Hz, H-12).

EXAMPLE 5

Preparation of (±) 8-Hydroxy-2,2,6,7-tetramethyl-3,4,7,8, 9,10-hexahydro-2H, 6H-dipyrano[2,3-f: 2,3-h]quinolin-10-one (Scheme V; 33)

Part 1: (±) 2,2,6,7-Tetramethyl-3,4,7,8,9,10-hexahydro-2H, 6H-dipyrano [2,3-f: 2,3-h]quinoline-8,10-dione (Scheme V; 27)

A solution of compound 6 (0.09 g, 0.276 mmol) in ethanol (1 ml) was treated with $PtO_2$ (0.009 g) and subjected to hydrogenation as described for 26. The residue obtained was purified through column chromatography (silica gel, 60–120 mesh, hexane ethyl acetate, 1: 6) afforded (±) 2,2,6,7-tetramethyl-3,4,7,8,9,10-hexahydro-2H, 6H-dipyrano [2,3-f: 2,3-h]quinoline-8,10-dione (27, 65 mg) in 72% yield as a gummy material.

1H NMR ($CDCl_3$, 200 MHz): δ 1.2 (d, 3H, J=6.9 Hz, $CH_3$), 1.42–1.48 (2s, 9H, $3CH_3$), 1.85 (t, 2H, J=6.9 Hz, $CH_2$), 2.54–2.72 (m, 3H, $CH_2$ and H-7), 4.68 (dq, 1 H, J=2.9 Hz, 6.2 Hz, H-6), 6.43 (d, 1H, J=9.8 Hz, H-11), 7.97 (d, 1H, J=10.0 Hz, H-12), 12.4 (br s, 1 H, NH).

Part 2: (±) 8-Hydroxy-2, 2, 6, 7-tetramethyl-3,4,7,8,9,10-hexahydro-2H, 6H-dipyrano[2,3-f: 2,3-h]quinolin-10-one ( Scheme V; 33)

Compound 27 (0.045 g, 0.437 mmol) in ethanol (0.5 ml) was treated with sodium borohydride (0.04 g, 137 mmol) as described for 7 The obtained after usual work up, purification by column chromatography (silica gel, 60–120 mesh, hexane:ethyl acetate, 1:9) afforded product (±) 8-hydroxy-2,2,6,7-tetramethyl-3,4,7,8,9,10-tetrahydro-2H, 6H-dipyrano[2,3-f: 2,3-h]quinoline-8,10-dione (33, 0.026 9) in 58% yield as a white solid.

$^1$H NMR ($CDCl_3$, 200 MHz): δ 1.09 (d, 3H, J=7.0 Hz, $CH_3$), 1.37 (s, 6H, $2CH_3$), 1.45 (d, 3H, J=7.0 Hz, $CH_3$), 1.8 (t, 2H, J=5.7 Hz, $CH_2$), 2.33 (dq, 1 H, J=2.9 Hz, 6.0 Hz, H-7), 2.64 (t, 2H, J=6.5 Hz, $CH_2$), 4.38 (dq, 1 H, J=2.9 Hz, 6.0 Hz, H-6), 5.44 (d, I H, J=6.2 Hz, H-8), 6.4 (d, 1H, J=10.4 Hz, H-1 1), 8.14 (d, 1H, J=10.4 Hz, H-12).

EXAMPLE 6

Preparation of (±) 8-Hydroxy-2,2,6,7,12-pentamethyl-3, 4,7,8,9,10-hexahydro-2H, 6H-dipyrano[2,3-f: Z 3-h]quinolin-10-one (Scheme V; 34)

Part 1: (±) 2,2,6,7,12-Pentamethyl-3,4,7,8,9,10-hexahydro-2H, 6H-dipyrano[2,3-f: 2,3-h]quinoline-8,10-dione (Scheme V; 28)

A solution of compound 17 (0.09 g, 0.265 mmol) in ethanol (1 mL) was subjected to hydrogenation with $PtO_2$ (0.009 g) as described for 26. Purification of residue by column chromatography (silica gel, 60–120 mesh, hexane : ethyl acetate, 8:1) afforded (±) 2,2,6,7,12-pentamethyl-3,4, 7,8,9,10-hexahydro-2H, 6H-dipyrano[2,3-f: 2,3-h]quinoline-8,10-dione (28, 0.016 g) in 89% yield as a white solid. M.P. 195–198° C. $^1$H NMR ($CDCl_3$, 200 MHz): δ 1.21 (d, 3H, J 7 7.0 Hz, $CH_3$), 1.39 (s, 3H, $CH_3$), 1.42 (s, 3H, $CH_3$), 1.53 (d, 3H, J=6.4 Hz, $CH_3$), 1.88 (t, 2H, J=6.6 Hz, $CH_2$), 2.46–2.78 (m, 6H, $CH_3$, $CH_2$ and H-7), 4.26 (dq, 1H, J=6.4 Hz, 11.4 Hz, H-6), 6.2 (s, 1H, H-1 1), 12.78 (brs, 1H, NH).

MSEI: m/z 341 ($M^+$, 52), 285 (61), 270 (24), 242 (24), 230 (48).

Part 2: (±) 8-Hydroxy-2,2,6,7,12-pentamethyl-3,4,7,8,9, 10-hexahydro-2H, 6H-dipyrano[2,3-f: 2,3 -h]quinolin-10-one (Scheme V; 34)

Compound 28 (0.1 g, 0.293 mmol) in ethanol (1 mL) was treated with sodium borohydride (0.011 g, 0.293 mmol) as described for 7 and the crude product was purified by column chromatography (silica gel, 60–120 mesh, hexane-:ethyl acetate, 9:1)to afford (±) 8-hydroxy-2,2,6,7,12-pentamethyl-3,4,7,8,9,10-hexahydro-2H, 6H-dipyrano[2, 3-f: 2,3-h]quinolin-10-one (34, 0.0729) in 72% yield as a white solid. M.P. 195–198° C.

$^1$H NMR ($CDCl_3$, 200 MHz): δ 1.18 (d, 3H, J=6.8 Hz, $CH_3$), 1.35 (s, 3H, $CH_3$), 1.4 (s, 3H, $CH_3$), 1.46 (d, 3H, J=6.8 Hz, $CH_3$), 1.77 (t, 2H, J=6.8 Hz, $CH_2$), 2.04 (dq,1 H, J=6.0 Hz, 11.5 Hz, H-7), 2.46–2.7 (m, 5H, $CH_3$ and $CH_2$), 3.94 (dq, 1 H, J=6.2 Hz, 11.8 Hz, H-6), 4.59 (d, 1H, J=8.8 Hz, H-8), 5.99 (s, 1H, H-11).

MSEI : m/z 343 ($M^+$, 9), 325 (80), 310 (75), 269 (27), 254 (100).

EXAMPLE 7

Preparation of (±) 8-Hydroxy-2,2,6,7,12-pentamethyl-3, 4,7,8,9,10-hexahydro-2H, 6H-dipyrano[2,3-f: 2,3-h]quinolin-10-one (Scheme V; 35)

Part 1: (±) 2,2,6,7,12-Pentamethyl-3,4,7,8,9,10-hexahydro-2H, 6H-dipyrano[2,3-f: 2,3h]quinoline-8,10-dione (Scheme V; 29)

Compound 19 (0.120 g) in ethanol (15 mL) was subjected to hydrogenation in presence of $PtO_2$ (0.012 9) as described for 26. Purification of the residue by column chromatography (silica gel, 60–120 mesh, hexane : ethyl acetate, 8:1) afforded, (±) 2,6,7,12-pentamethyl-3,4,7,8,9,10-hexahydro-2H, 6H-dipyrano[2,3-f: 2,3-h]quinoline-8,10-dione (29, 0.099 9) in 83% yield as a white solid. M.P. 145–146° C.

$^1$H NMR (CDCl$_3$, 200 MHz): δ 1.14 (d, 3H, J=6.8 Hz, CH$_3$), 1.36–1.58 (m, 9H, 3CH$_3$), 1.82 (t, 2H, J=6.0 Hz, CH$_2$), 2.46–2.73 (m, 6H, CH$_3$, CH$_2$ and H-7), 4.64 (dq, 1H, J=2.9 Hz, 6.1 Hz, H-6), 6.22 (s, 1H, H-11), 12.8 (brs, 1H, NH).

Part 2: (±) 8-Hydroxy-2,2,6,7,12-pentamethyl-3,4,7,8,9, 10-hexahydro-2H, 6H-dipyrano[2,3-f: 2,3-h]quinolin-10-one (Scheme V; 35)

Compound 29 (0.1 g, 0.293 mmol) in ethanol (1 mL) was treated with sodium borohydride (0.011 g, 0.293 mmol) as described for 7 and purification of the crude product by column chromatography (silica gel, , 60–120 mesh, hexane:ethyl acetate, 1:8) afforded (±) 8-hydroxy-2,2,6,7, 12-pentamethyl-3,4,7,8,9,10-hexahydro-2H, 6H-dipyrano [2,3-f: 2,3-h]quinolin-10-one (35, 0.065 g) in 65% yield as a white solid.

M.P. 183–185° C.

$^1$H NMR (CDCl$_3$, 200 MHz): δ 1.08 (d, 3H, J=6.8 Hz, CH$_3$), 1.24–1.5 (m, 9H, 3CH$_3$), 1.76 (t, 2H, J=6.9 Hz, CH$_2$), 2.33 (dq, 1H, J=3.0 Hz, 6.6 Hz, H-7), 2.52–2.75 (m, 5H,CH$_3$ and CH$_2$), 4.35 (dq, 1 H, J=2.9 Hz, 6.4 Hz, H-6), 5.32 (d, 1 H, J=3.9Hz,H-8), 6.22 (s,1 H,H-11).

EXAMPLE 8

Preparation of (±) 8-Hydroxy-2,2,6,7-tetramethyl-12-propyl-3,4,7,8,9,10-hexahydro-2H, 6H-dipyrano[2,3-f: 2,3-h]quinolin-10-one (Scheme V; 36) Part 1: (±) 2,2,6,7-Tetramethyl-12-propyl-3,4,7,8,9,10-hexahydro-2H, 6H-dipyrano[2, 3-f: 2,3-h]quinoline-8,10-dione (Scheme V; 30)

Compound 18 (0.13 g, 0.354 mmol) in ethanol (2.5 mL) on hydrogenation with PtO$_2$ (0.013 g) as described for 26 afforded (±) 2,2,6,7-tetramethyl-12-propyl-3,4,7,8,9,10-hexahydro-2H, 6H-dipyrano[2,3-f: 2,3-h]quinoline-8,10-dione (30, 0.11 g) in 85% yield as a white solid. M.P. 141–142° C.

$^1$H NMR (CDCl$_3$, 200 MHz): δ 1.0 (t, 3H, J=7.2 Hz, CH$_3$), 1.24 (d, 3H, J=7.0 Hz,CH$_3$), 1.44 (s, 3H, CH$_3$), 1.45 (s, 3H, CH$_3$), 1.6 (d, 3H, J=7.0 Hz, CH$_3$),1.62–1.70 (m,2H, CH$_2$), 1.86 (t, 2H, J=6.5 Hz, CH$_2$), 2.6 (dq, 1 H, J=6.5 Hz, 11.5 Hz, H-7), 2.7 (t, 2H, J=6.9 Hz, CH$_2$), 2.92 (t, 2H, J=7.2 Hz, CH$_2$ ), 4.28 (dq, 1 H, J=6.4 Hz, 11.4 Hz, H-6), 6.22 (s, 1H, H-11), 12.9 (brs, 1H, NH).

MSEI: m/z 369 (M$^+$ 100), 354 (10), 341 (15), 296 (40), 270 (15) 258 (36)

Part 2: (±) 8-Hydroxy-2,2,6,7-tetramethyl-12-propyl-3,4, 7,8,9,10-hexahydro-2H, 6H-dipyrano[2,3-f: 2,3-h]quinolin-10-one (Scheme V; 36)

Compound 30 (0.09 g, 0.244 mmol) in ethanol (1 mL) was treated with sodium borohydride (0.009 g, 0.244 mmol) as described for 7 and the residue obtained on usual work up, after purification by column chromatography (silica gel, 60–120 mesh, hexane:ethyl acetate, 1:9) afforded (±) 8-hydroxy-2,2,6,7-tetramethyl-12-propyl-3,4,7,8,9,10-hexahydro-2H, 6H-dipyrano[2, 3-f: 2, 3-h]quinolin-1 0-one (36, 0.07 g) in 78% yield as a white solid. M.P. 185–188° C.

$^1$ H NMR (CDCl$_3$, 200 MHz): 8 1.0 (t, 3H, J=7.4 Hz, CH$_3$), 1.2 (d, 3H, J=7.1 Hz,CH$_3$), 1.46 (s, 6H, 2CH$_3$), 1.5 (d, 3H, J=7.0 Hz, CH$_3$), 1.54–1.72 (m, 2H, CH$_2$), 1.8 (t, 2H, J=7.0 Hz, CH$_2$), 1.9–2.12 (m, 1H, H-7), 2.65 (t, 2H, J=7.2 Hz,CH$_2$), 2.8–3.15 (m, 2H,CH$_2$), 3.95 (dq, 1 H, J=6.4 Hz, 11.9 Hz, H-6), 4.68 (d, 1H, J=8.6 Hz, H-8), 6.2 (s, 1H, H-1 1).

MSEI: m/z 371 (M$^+$, 13), 353 (M$^+$, -H$_2$0, 57), 338 (40), 298 (39), 287 (100).

EXAMPLE 9

Preparation of (±) 8-Hydroxy-2,2,6,7-tetramethyl-12-propyl-3,4,7,8,9,10-hexahydro-2H, 6H-dipyrano[2, 3-f: 2,3-h]quinolin-10-one (Scheme V; 37)

Part 1: (±) 2,2,6,7-Tetramethyl-12-propyl-3,4,7,8,9,10-hexahydro-2H, 6H-dipyrano[2,3-f: 2,3-h]quinolin-8, 1 0-dione (Scheme V; 31)

Compound 20 (0.16 g, 0.436 mmol) in ethanol (3 mL) was subjected to hydrogenation with PtO$_2$ (0.016 g) as described for 26 and purification of the residue by column chromatography (silica gel, 60–120 mesh, hexane : ethyl acetate, 7:3) afforded (±) 2.2,6,7-tetramethyl-12-propyl-(6R, 7S)-3,4,7,8,9,10-hexahydro-2H,6H-dipyrano[2,3-f:2,3-h] quinolin-8,10-dione (31, 0.115 g) in 71.5% yield as a white solid. M.P. 150–151° C.

$^1$H NMR (CDCl$_3$, 200 MHz): δ 1.02 (t, 3H, J=6.8 Hz, CH$_3$), 1.2 (d, 3H; J=7.0 Hz,CH$_3$), 1.45 (s, 6H, 2CH$_3$), 1.58–1.72 (m, 2H, CH$_2$),1.87 (t, 2H, J=6.8 Hz, CH$_2$), 2.57–2.78 (m, 3H, CH$_2$ and H-7), 2.84 (t, 2H, J=7.2 Hz, CH$_2$), 4.67 (dq,1 H, J=3.0 Hz, 6.0 Hz, H-6), 6.26 (s, 1H, H-11), 12.95 (brs, 1H, NH).

Part 2: (±) 8-Hydroxy-2,2,6,7-tetramethyl-12-propyl-3,4, 7,8,9,10-hexahydro-2H, 6H-dipyrano[2,3-f: 2,3-h]quinolin-10-one (Scheme V; 37)

Compound 31 (0.09 9, 0.244 mmol) in ethanol (1 mL) was treated with sodium borohydride (0.009 g, 0.244 mmol) as described for 7 and after purification of the obtained residue by column chromatography (silica gel, 60–120 mesh, hexane:ethyl acetate, 1:9) afforded (±) 8-hydroxy-2, 2,6,7-tetramethyl-12-propyl-3,4,7,8,9,10-hexahydro-2H, 6H-dipyrano[2, 3-f: 2, 3-h]quinolin-10-one (37, 0.08 g) in 88% yield as a white solid. M.P. 215–217° C.

$^1$H NMR (CDCl$_3$, 200 MHz): δ 1.01 (t, 3H, J=7.2 Hz, CH$_3$), 1.1 (d, 2H, J=6.9 Hz,CH$_3$), 1.39 (s, 6H, 2CH$_3$), 1.43 (d, 3H, J=6.0 Hz, CH$_3$), 1.55–1.66 (m, 2H, CH$_2$),1.86 (t, 2H, J=7.2 Hz, CH$_3$), 2.23–2.4 (m, 1 H, H-7), 2.62 (t, 2H, J=6.9 Hz, CH$_2$), 3.1 (t, 2H, J=6.7 Hz, CH$_2$), 4.37 (dq, 1H, J=3.2 Hz, 6.6 Hz, H-6), 5.36 (d, 1H, J=6.2 Hz, H-8), 6.17 (s, 1H, H-11).

What is claimed is:

1. A dipyrano-quinolinone class of compounds having the general formula I:

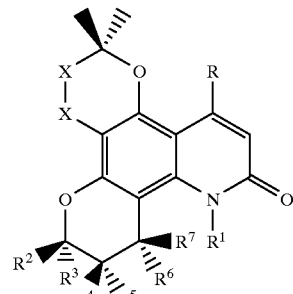

I wherein R is hydrogen, C$_1$–C$_{10}$ alkyl group optionally substituted with halo, hydroxyl, amino, alkylamino, cyano, alkoxy, aryloxy and nitro groups, C$_1$–C$_{10}$ alkenyl group with one or more double bonds optionally substituted with halo, hydroxyl, amino, alkylamino, cyano, alkoxy, aryloxy and nitro groups, C$_1$–C$_{10}$ alkynyl group with one or more triple bonds optionally substituted with halo, hydroxyl, amino, alkylamino, cyano, alkoxy, aryloxy and nitro groups, aryl, hetero aryl, carbocyclic aryl, alkyl aryl, acyclic compounds, C-1 to C-6 alkyl with terminal dialkyl amino group, thio alkyl, hydroxy alkyl groups;

R$^1$ is H, lower dialkyl amino alkyls wherein the alkyl portions are chosen from ethyl, propyl, and other alkyl groups or α or β-amino acid moieties, hydroxy alkyl groups having optionally substituted about C-1 to C-10 carbons, acid amides such as aliphatic acids, aromatic acids, sulphonic acids, trihalo acids;

x—x is either a carbon-carbon single bond or a carbon-carbon double bond;

$R^2$ and $R^3$, $R^4$ and $R^5$ are each independently hydrogen or methyl there by resulting in the cis and trans diastereomers as well as enantiomers;

$R^6$ and $R^7$ are each independently hydrogen or hydroxy/—$OR^8$, where $R^8$ is independently allyl, aryl alkyl, amino alkyl, hydroxy alkyl with C-1 to C-10 carbons, sugars which include mono saccharides both in the furanose form as well as pyranose form, amino sugars, disaccharides, amino acids, small peptides, thereby resulting the cis and trans diastereomers as well as enantiomers.

2. A dipyrano-quinolinone class of compounds as claimed in claim 1 wherein said compounds having a structural formula as shown herebelow:

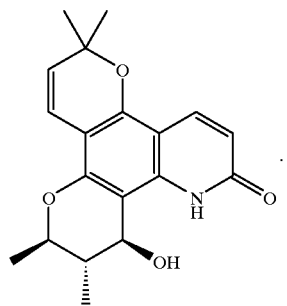

3. A dipyrano-quinoline class of compounds as claimed in claim 1 wherein said compounds having a structural formula as shown herebelow:

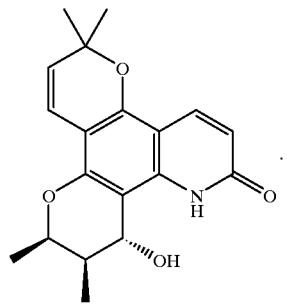

4. A dipyrano-quinolinone class of compounds as claimed in claim 1 wherein said compounds having a structural formula as shown herebelow:

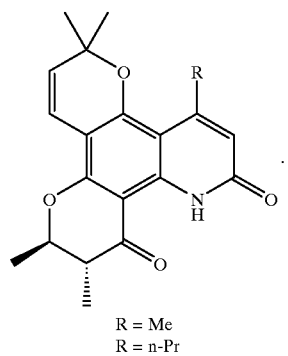

R = Me
R = n-Pr

5. A dipyrano-quinolinone class of compounds as claimed in claim 1 wherein said compounds having a structural formula as shown herebelow:

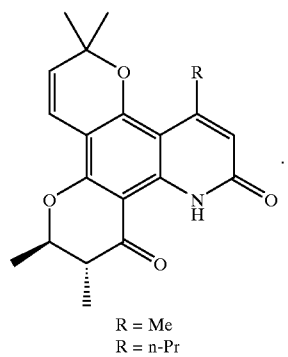

R = Me
R = n-Pr

6. A dipyrano-quinolinone class of compounds as claimed in claim 1 wherein said compounds having a structural formula as shown herebelow:

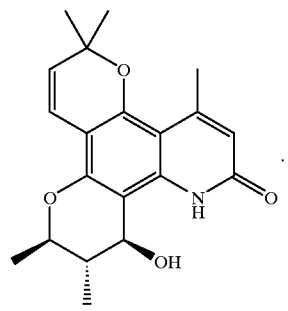

7. A dipyrano-quinolinone class of compounds as claimed in claim 1 wherein said compounds having a structural formula as shown herebelow:

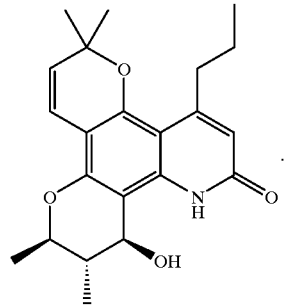

8. A dipyrano-quinolinone class of compounds as claimed in claim 1 wherein said compounds having a structural formula as shown herebelow:

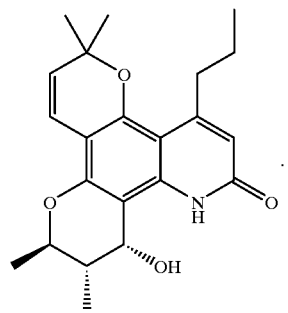

9. A dipyrano-quinolinone class of compounds as claimed in claim 1 wherein said compounds having a structural formula as shown herebelow:

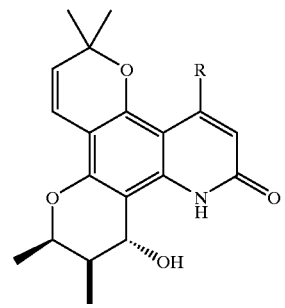

R = Me
R = n-Pr

10. A dipyrano-quinolinone class of compounds as claimed in claim 1 wherein said compounds having a structural formula as shown herebelow:

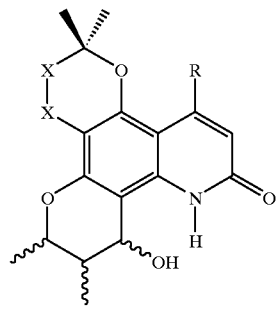

11. A dipyrano-quinolinone class of compounds as claimed in claim I wherein said compounds having a structural formula as shown herebelow:

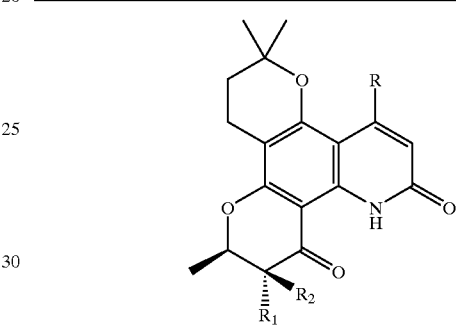

| | | |
|---|---|---|
| R = H, | $R_1$ = Me, | $R_2$ = H |
| R = H, | $R_1$ = H, | $R_2$ = Me |
| R = Me, | $R_1$ = Me, | $R_2$ = H |
| R = Me, | $R_1$ = H, | $R_2$ = Me |
| R = n-Pr, | $R_1$ = Me, | $R_2$ = H |
| R = n-Pr, | $R_1$ = H, | $R_2$ = Me. |

12. A dipyrano-quinolinone class of compounds as claimed in claim 1 wherein said compounds having a structural formula as shown herebelow:

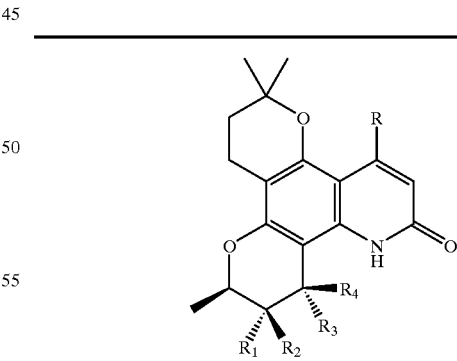

| | | | | |
|---|---|---|---|---|
| R = H, | $R_1$ = Me, | $R_2$ = H, | $R_3$ = H, | $R_4$ = OH |
| R = H, | $R_1$ = H, | $R_2$ = Me, | $R_3$ = OH, | $R_4$ = H |
| R = Me, | $R_1$ = Me, | $R_2$ = H, | $R_3$ = H, | $R_4$ = OH |
| R = Me, | $R_1$ = H, | $R_2$ = Me, | $R_3$ = OH, | $R_4$ = H |
| R = n-Pr, | $R_1$ = Me, | $R_2$ = H, | $R_3$ = H, | $R_4$ = OH |
| R = n-Pr, | $R_1$ = H, | $R_2$ = Me, | $R_3$ = OH, | $R_4$ = H. |

13. A method for preparation of a 'dipyrano-quinolinone' class of compounds having a structure as claimed in claim 1, which are useful as anti-viral agents, said process comprising:
   a) reacting substituted aniline with an acid chloride or 1,3-dioxinone to provide the amides,
   b) cyclizing amides in the presence of acids to provide quinolinones and cleaving of methoxyl group using Lewis acid,
   c) reacting quinolinone with tigloyl chloride to provide the acylation products,
   d) cyclizing the acylation products in the presence of acid or base to provide the chromanone ring, obtaining the product as a racemic mixture and resolving into isomers,
   e) reacting the chromanone with substituted propargyl chloride to provide chromanone,
   f) reacting the chromanone with suitable reducing agent to provide the new chemical entities the 'dipyrano-quinolinone' class of compounds, and if desired,
   g) hydrogenating the chromene ring to give the dihydro derivatives, and
   h) reducing the dihydro keto derivatives with reducing agents to get the dihydro alko analogues.

14. A method of claim 13 wherein the substituted aniline is a 3,5-dimethoxy aniline.

15. A method of claim 13 wherein acid chloride is cinnamoyl chloride.

16. A method of claim 13 wherein 1,3-dioxinone is an alkyl substituted 1,3-dioxinone ring system, wherein alkyl is a methyl or n-propyl.

17. A method of claim 13 wherein the amide is subjected to cyclisation under acidic conditions.

18. A method of claim 13 wherein in the ether is cleaved using Lewis acid reaction conditions.

19. A method of claim 13 wherein the phenol is acylated with acid chloride such as tigloyl chloride.

20. A method of claim 13 wherein the acylated phenol is cyclised under acidic conditions.

21. A method of claim 13 wherein the acylated phenol is cyclised under basic conditions.

22. A method of claim 13 wherein in the cyclisation produces one of the diastereo isomers, the trans isomer in at least about 60 percent relative to the other isomer, the cis isomer.

23. A method of claim 13 wherein in the phenol is cyclised with substituted propargyl chloride.

24. A method of claim 13 wherein the diastereomeric mixture is resolved into pure trans and cis isomers.

25. A method of claim 24 wherein the trans isomer is present in at least about 70 percent relative to the cis isomer.

26. A method of claim 24 wherein the trans isomer (R=H) is reduced with suitable reducing agent.

27. A method of claim 24 wherein the cis isomer (R=H) is reduced with suitable reducing agent to produce a racemic mixture of compounds.

28. A method of claim 24 wherein the trans isomer (R=Me) is reduced with a suitable reducing agent to produce diastereomeric mixtures.

29. A method of claim 24 wherein the cis isomer (R=Me) is reduced with a suitable reducing agent to produce a mixture of alcohols.

30. A method of claim 24, wherein trans isomer (R=n-Pr) is reduced with a suitable reducing agent to produce diastereomeric mixture of compounds.

31. A method of claim 29 wherein the reduction produces a trans stereoisomer that is present in at least 70 percent relative to the cis isomer.

32. A method of claim 29, wherein cis isomer (R=n-Pr) is reduced with a suitable reducing agent to produced a racemic mixture of compounds.

33. A method of claim 29, wherein cis ketone (R=H) is hydrogenated to dihydro derivatives.

34. A method of claim 29, wherein trans ketone (R=H) is hydrogenated to dihydro derivatives.

35. A method of claim 33 wherein the cis dihydro derivative (R=H) is reduced with a suitable reducing agent to produce alcohols.

36. A method of claim 33 wherein the trans dihydro derivative (R=H) is reduced with a suitable reducing agent to produce alcohols.

37. A method of claim 26, wherein trans ketone (R=Me) is hydrogenated to dihydro derivatives.

38. A method of claim 26, wherein cis ketone (R=Me) is hydrogenated to dihydro derivatives.

39. A method of claim 37, wherein the trans dihydro derivative (R=Me) is reduced with a suitable reducing agent to produce alcohols.

40. A method of claim 38, wherein the cis dihydro derivative (R=Me) is reduced with a suitable reducing agent to produce alcohols.

41. A method of claim 39, wherein trans ketone (R=n-Pr) is hydrogenated to dihydro derivatives.

42. A method of claim 39, wherein cis ketone (R=n-Pr) is hydrogenated to dihydro derivatives.

43. A method of claim 39, wherein in the trans dihydro derivative (R=n-Pr) is hydrogenated to dihydro derivatives.

44. A method of claim 39, wherein the cis dihydro derivative (R=n-Pr) is reduced with a suitable reducing agent to produce alcohols.

45. A method of testing a compound of formula III

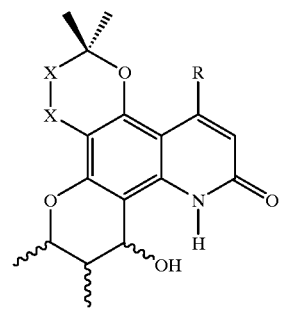

III for protection against HIV infection, comprising screening said compound for anti-HIV activity.

46. A method of claim 45, wherein the compound is tested in vitro against HIV-1.

47. A method of claim 45, wherein the preliminary screening indicated potential anti-HIV activity.

48. A method of claim 45, wherein the protection against HIV infection is comparable and better relatively to known calanolides.

49. A method of claim 45, wherein the therapeutic index value is comparable to the existing substances.

50. A method of claim 45, wherein the compound has envisaged advantages of more solubility relatively to calanolides.

51. A method of claim 45, wherein the compound has envisaged advantages of more stability relatively to calanolides.

* * * * *

UNITED STATES PATENT AND TRADEMARK OFFICE
CERTIFICATE OF CORRECTION

PATENT NO. : 6,191,279 B1
DATED : February 20, 2001
INVENTOR(S) : Mukund Keshao Gurjar et al.

It is certified that error appears in the above-identified patent and that said Letters Patent is hereby corrected as shown below:

Title page,
Item [73], Assignee, "Science" should read -- Scientific --; and "New Delhi, IN (US)" should read -- New Delhi (IN) --.

Item [57], ABSTRACT,
Line 5, after "C-10", insert a comma;
Line 6, "double bounds" should read -- double bonds --;
Line 12, before "b-amino", insert -- a or --;
Line 15, after "sulphonic acids", insert a comma; and
Line 20, "there by" should read -- thereby --.

Column 25, claim 1,
Line 8, "there by" should read -- thereby --.

Column 28, claim 11,
Line 16, "claim I" should read -- claim 1 --.

Column 29, claim 17,
Line 32, "cyclisation" should read -- cyclization --.

Column 29, claim 20,
Line 38, "cyclised" should read -- cyclized --.

Column 29, claim 21,
Line 40, "cyclised" should read -- cyclized --.

UNITED STATES PATENT AND TRADEMARK OFFICE
CERTIFICATE OF CORRECTION

PATENT NO. : 6,191,279 B1
DATED : February 20, 2001
INVENTOR(S) : Mukund Keshao Gurjar et al.

It is certified that error appears in the above-identified patent and that said Letters Patent is hereby corrected as shown below:

Column 29, claim 22,
Line 41, "cyclisation" should read -- cyclization --.

Column 29, claim 23,
Line 45, "cyclised" should read -- cyclized --.

Column 30, claim 32,
Line 2, "to produced" should read -- to produce --.

Signed and Sealed this

Twenty-fifth Day of December, 2001

Attest:

Attesting Officer

JAMES E. ROGAN
*Director of the United States Patent and Trademark Office*